United States Patent
Russell

(10) Patent No.: US 11,868,527 B2
(45) Date of Patent: Jan. 9, 2024

(54) EYE TRACKING USING ALTERNATE SAMPLING

(71) Applicant: Magic Leap, Inc., Plantation, FL (US)

(72) Inventor: Andrew Ian Russell, Weston, FL (US)

(73) Assignee: Magic Leap, Inc., Plantation, FL (US)

( * ) Notice: Subject to any disclaimer, the term of this patent is extended or adjusted under 35 U.S.C. 154(b) by 0 days.

(21) Appl. No.: 17/925,139

(22) PCT Filed: Jul. 21, 2021

(86) PCT No.: PCT/US2021/042518
§ 371 (c)(1),
(2) Date: Nov. 14, 2022

(87) PCT Pub. No.: WO2022/020434
PCT Pub. Date: Jan. 27, 2022

(65) Prior Publication Data
US 2023/0185369 A1    Jun. 15, 2023

Related U.S. Application Data

(60) Provisional application No. 63/058,383, filed on Jul. 29, 2020, provisional application No. 63/055,807, filed on Jul. 23, 2020.

(51) Int. Cl.
*G06F 3/01* (2006.01)
*G02B 27/01* (2006.01)
(Continued)

(52) U.S. Cl.
CPC ......... *G06F 3/013* (2013.01); *G02B 27/0093* (2013.01); *G02B 27/0172* (2013.01); *G06T 7/20* (2013.01); *G06T 2207/30201* (2013.01)

(58) Field of Classification Search
CPC . G06F 3/013; G02B 27/0093; G02B 27/0172; G06T 7/20; G06T 2207/30201
See application file for complete search history.

(56) References Cited

U.S. PATENT DOCUMENTS 10,473,042 B2    11/2019    Abei et al.
10,521,025 B2    12/2019    Powderly et al.
(Continued)

OTHER PUBLICATIONS

International Search Report and Written Opinion, dated Nov. 12, 2021, in PCT/US2021/042518 (11 pages).

*Primary Examiner* — Xuemei Zheng
(74) *Attorney, Agent, or Firm* — Fish & Richardson P.C.

(57) ABSTRACT

An eye tracking system can include a first camera configured to capture a first plurality of visual data of a right eye at a first sampling rate. The system can include a second camera configured to capture a second plurality of visual data of a left eye at a second sampling rate. The second plurality of visual data can be captured during different sampling times than the first plurality of visual data. The system can estimate, based on at least some visual data of the first and second plurality of visual data, visual data of at least one of the right or left eye at a sampling time during which visual data of an eye for which the visual data is being estimated are not being captured. Eye movements of the eye based on at least some of the estimated visual data and at least some visual data of the first or second plurality of visual data can be determined.

27 Claims, 11 Drawing Sheets

(51) Int. Cl.
    *G06T 7/20*           (2017.01)
    *G02B 27/00*        (2006.01)

(56) References Cited

U.S. PATENT DOCUMENTS

| | | |
|---|---|---|
| 10,559,127 B2 | 2/2020 | Wei et al. |
| 2004/0174496 A1 | 9/2004 | Ji et al. |
| 2014/0002587 A1 | 1/2014 | Aguren |
| 2015/0016777 A1 | 1/2015 | Abovitz et al. |
| 2015/0178939 A1 | 6/2015 | Bradski et al. |
| 2016/0270656 A1 | 9/2016 | Samec et al. |
| 2018/0342066 A1 | 11/2018 | Mallinson et al. |
| 2019/0222830 A1 | 7/2019 | Edwin et al. |
| 2019/0243448 A1 | 8/2019 | Miller et al. |
| 2019/0272028 A1* | 9/2019 | Hong .................. G06T 7/70 |
| 2020/0026350 A1 | 1/2020 | Eash et al. |
| 2021/0173479 A1* | 6/2021 | Klingström ............ G06V 40/20 |
| 2023/0239586 A1* | 7/2023 | Agaoglu ............. H04N 23/611 348/78 |

* cited by examiner

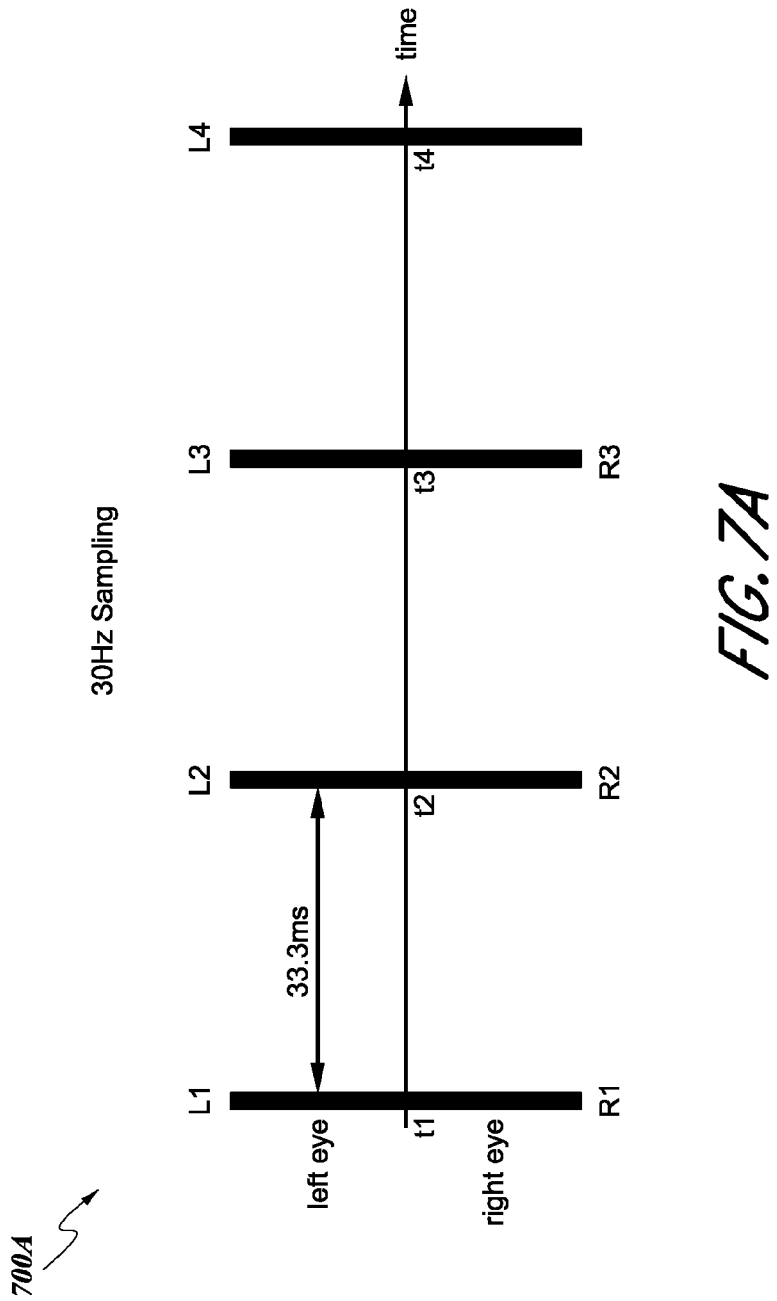

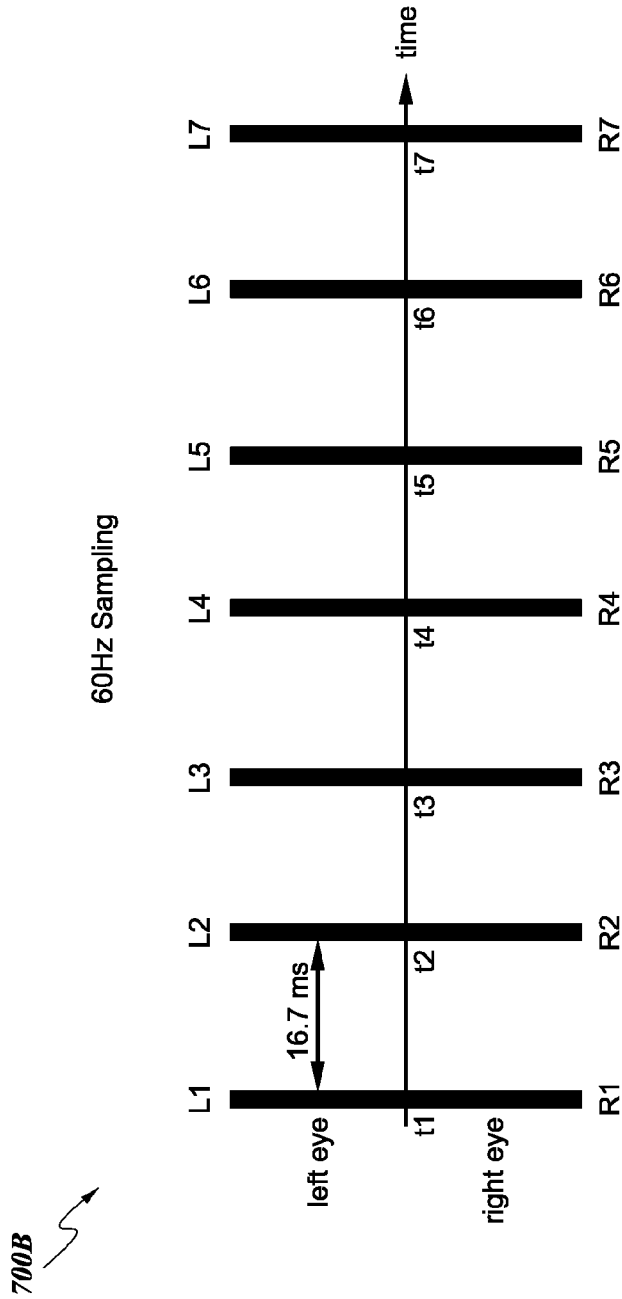

EYE TRACKING USING ALTERNATE SAMPLING

CROSS-REFERENCE TO RELATED APPLICATIONS

This application is a National Stage Application of International Application No. PCT/US2021/042518, filed Jul. 21, 2021, which claims priority to U.S. Provisional Patent Application No. 63/055,807 filed on Jul. 23, 2020 and U.S. Provisional Patent Application No. 63/058,383 filed on Jul. 29, 2020, each of which is incorporated by reference in its entirety.

FIELD

The present disclosure relates to display systems, virtual reality, and augmented reality imaging and visualization systems.

BACKGROUND

Modern computing and display technologies have facilitated the development of systems for so called "virtual reality", "augmented reality", or "mixed reality" experiences, wherein digitally reproduced images or portions thereof are presented to a user in a manner wherein they seem to be, or may be perceived as, real. A virtual reality, or "VR", scenario typically involves presentation of digital or virtual image information without transparency to other actual real-world visual input; an augmented reality, or "AR", scenario typically involves presentation of digital or virtual image information as an augmentation to visualization of the actual world around the user; a mixed reality, or "MR", related to merging real and virtual worlds to produce new environments where physical and virtual objects co-exist and interact in real time. As it turns out, the human visual perception system is very complex, and producing a VR, AR, or MR technology that facilitates a comfortable, natural-feeling, rich presentation of virtual image elements amongst other virtual or real-world imagery elements is challenging. Systems and methods disclosed herein address various challenges related to VR, AR and MR technology.

SUMMARY

An eye tracking system can include a first camera configured to capture a first plurality of visual data of a right eye of a user at a first sampling rate and a second camera configured to capture a second plurality of visual data of a left eye of the user at a second sampling rate. The second plurality of visual data can be captured during different sampling times than the first plurality of visual data. The system can include processing electronics configured to, based on at least some visual data of the first and second plurality of visual data, estimate visual data of at least one of the right or left eye at a sampling time during which visual data of an eye for which the visual data is being estimated are not being captured. The processing electronics can be configured to determine eye movement of the eye based on at least some of the estimated visual data and at least some visual data of the first or second plurality of visual data.

In various implementations, a combined sampling rate of the first and second cameras can be an aggregate of the first and second sampling rates. The first sampling rate and/or second sampling rate can be 30 Hz, 40 Hz, 60 Hz, 100 Hz, 120 Hz, or another sampling rate. The first and second cameras can be configured to alternate capture of the first and second pluralities of visual data. The processing electronics can be configured to estimate the visual data based on a determination of difference between at least one visual data of the first plurality of visual data of the right eye and at least one visual data of the second plurality of visual data of the left eye. The processing electronics can be configured to estimate the visual data of the right or left eye based on filtering the difference.

In some implementations, a wearable display system can include the eye tracking system of any of the preceding paragraph and/or any of the eye tracking systems described herein and a display configured to present virtual content. The processing electronics can cause the display to present the virtual content based on the eye movement. The display can be a head mounted display.

Details of one or more implementations of the subject matter described in this specification are set forth in the accompanying drawings and the description below. Other features, aspects, and advantages will become apparent from the description, the drawings, and the claims. Neither this summary nor the following detailed description purports to define or limit the scope of the inventive subject matter.

BRIEF DESCRIPTION OF THE DRAWINGS

FIG. 5A schematically illustrates an example coordinate system for determining an eye pose of an eye

FIGS. 7A and 7B are graphs that illustrate capturing visual data of a left eye and a right eye.

Figure 1:
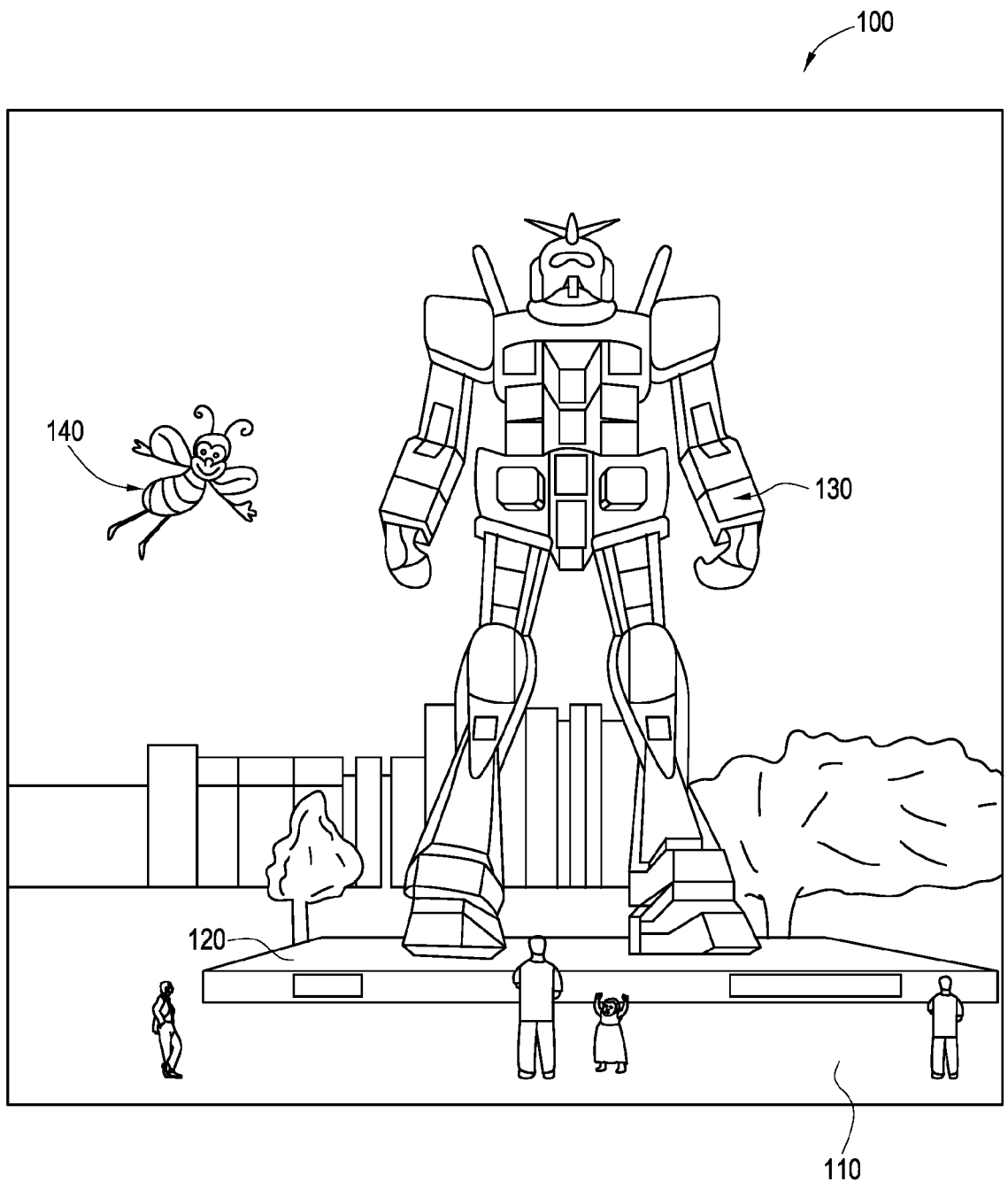
FIG. 1 depicts an illustration of a mixed reality scenario with certain virtual reality objects, and certain physical objects viewed by a person.

Throughout the drawings, reference numbers may be re-used to indicate correspondence between referenced elements. The drawings are provided to illustrate example embodiments described herein and are not intended to limit the scope of the disclosure.

DETAILED DESCRIPTION

Reference will now be made to the drawings, in which like reference numerals refer to like parts throughout. Unless indicated otherwise, the drawings are schematic not necessarily drawn to scale.

Examples of 3D Display of a Wearable System

A wearable system (also referred to herein as an augmented reality (AR) system) can be configured to present 2D or 3D virtual images to a user. The images may be still images, frames of a video, or a video, in combination or the like. At least a portion of the wearable system can be implemented on a wearable device that can present a VR, AR, or MR environment, alone or in combination, for user interaction. The wearable device can be used interchangeably as an AR device (ARD). Further, for the purpose of the present disclosure, the term "AR" is used interchangeably with the term "MR".

FIG. 1 depicts an illustration of a mixed reality scenario with certain virtual reality objects, and certain physical objects viewed by a person. In FIG. 1, an MR scene 100 is depicted wherein a user of an MR technology sees a real-world park-like setting 110 featuring people, trees, buildings in the background, and a concrete platform 120. In addition to these items, the user of the MR technology also perceives that he "sees" a robot statue 130 standing upon the real-world platform 120, and a cartoon-like avatar character 140 flying by which seems to be a personification of a bumble bee, even though these elements do not exist in the real world.

In order for the 3D display to produce a true sensation of depth, and more specifically, a simulated sensation of surface depth, it may be desirable for each point in the display's visual field to generate an accommodative response corresponding to its virtual depth. If the accommodative response to a display point does not correspond to the virtual depth of that point, as determined by the binocular depth cues of convergence and stereopsis, the human eye may experience an accommodation conflict, resulting in unstable imaging, harmful eye strain, headaches, and, in the absence of accommodation information, almost a complete lack of surface depth.

VR, AR, and MR experiences can be provided by display systems having displays in which images corresponding to a plurality of depth planes are provided to a viewer. The images may be different for each depth plane (e.g., provide slightly different presentations of a scene or object) and may be separately focused by the viewer's eyes, thereby helping to provide the user with depth cues based on the accommodation of the eye required to bring into focus different image features for the scene located on different depth plane or based on observing different image features on different depth planes being out of focus. As discussed elsewhere herein, such depth cues provide credible perceptions of depth.

Figure 2:
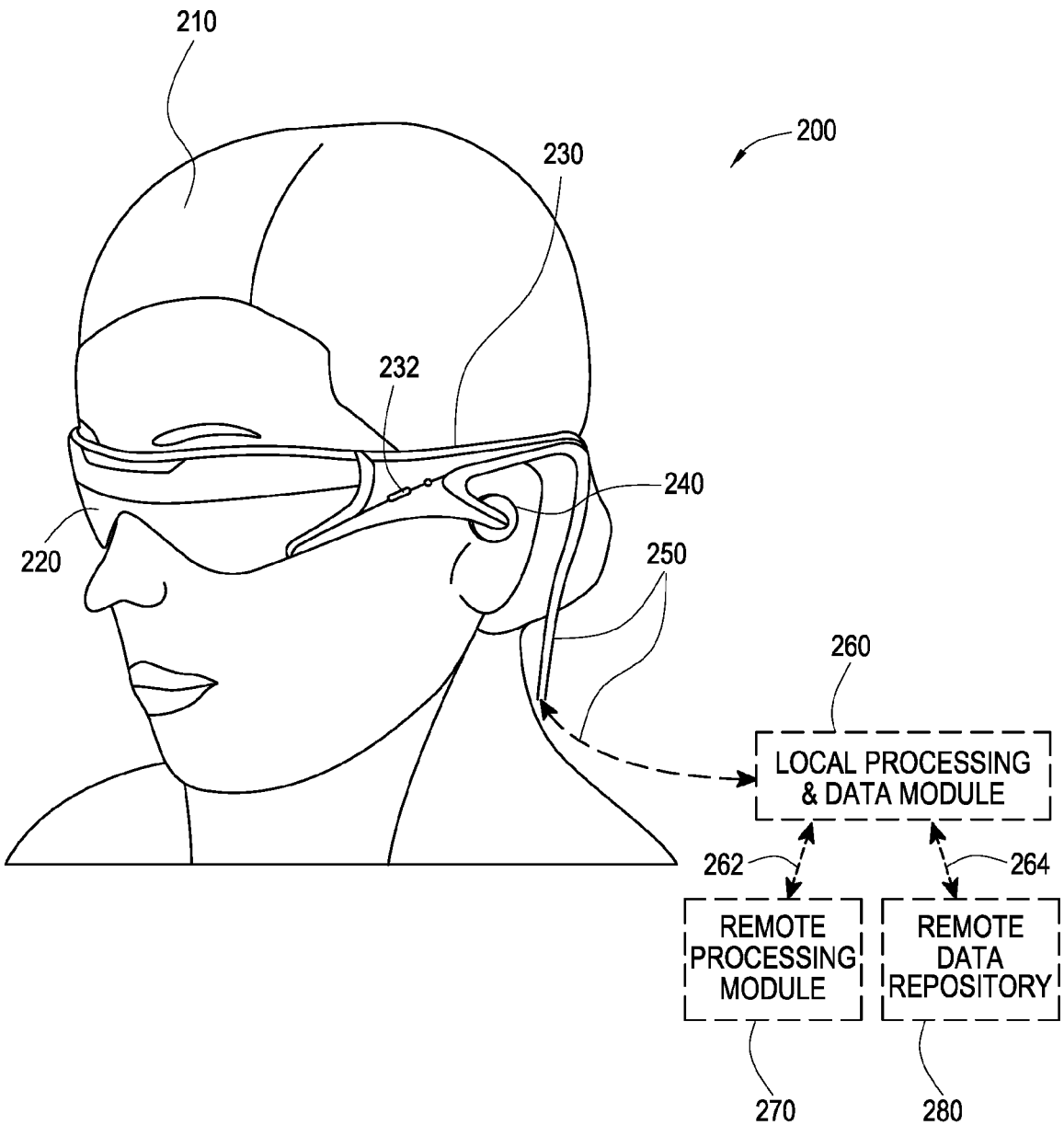
FIG. 2 schematically illustrates an example of a wearable system.

FIG. 2 illustrates an example of wearable system 200 which can be configured to provide an AR/VR/MR scene. The wearable system 200 can also be referred to as the AR system 200. The wearable system 200 includes a display 220, and various mechanical and electronic modules and systems to support the functioning of display 220. The display 220 may be coupled to a frame 230, which is wearable by a user, wearer, or viewer 210. The display 220 can be positioned in front of the eyes of the user 210. The display 220 can present AR/VR/MR content to a user. The display 220 can comprise a head mounted display (HMD) that is worn on the head of the user.

In some embodiments, a speaker 240 is coupled to the frame 230 and positioned adjacent the ear canal of the user (in some embodiments, another speaker, not shown, is positioned adjacent the other ear canal of the user to provide for stereo/shapeable sound control). The display 220 can include an audio sensor (e.g., a microphone) 232 for detecting an audio stream from the environment and capture ambient sound. In some embodiments, one or more other audio sensors, not shown, are positioned to provide stereo sound reception. Stereo sound reception can be used to determine the location of a sound source. The wearable system 200 can perform voice or speech recognition on the audio stream.

The wearable system 200 can include an outward-facing imaging system 464 (shown in FIG. 4) which observes the world in the environment around the user. The wearable system 200 can also include an inward-facing imaging system 462 (shown in FIG. 4) which can track the eye movements of the user. The inward-facing imaging system may track either one eye's movements or both eyes' movements. The inward-facing imaging system 462 may be attached to the frame 230 and may be in electrical communication with the processing modules 260 or 270, which may process image information acquired by the inward-facing imaging system to determine, e.g., the pupil diameters or orientations of the eyes, eye movements or eye pose of the user 210. The inward-facing imaging system 462 may include one or more cameras. For example, at least one camera may be used to image each eye. The images acquired by the cameras may be used to determine pupil size or eye pose for each eye separately, thereby allowing presentation of image information to each eye to be dynamically tailored to that eye.

As an example, the wearable system 200 can use the outward-facing imaging system 464 or the inward-facing imaging system 462 to acquire images of a pose of the user. The images may be still images, frames of a video, or a video.

The display 220 can be operatively coupled 250, such as by a wired lead or wireless connectivity, to a local data processing module 260 which may be mounted in a variety of configurations, such as fixedly attached to the frame 230, fixedly attached to a helmet or hat worn by the user, embedded in headphones, or otherwise removably attached to the user 210 (e.g., in a backpack-style configuration, in a belt-coupling style configuration).

The local processing and data module 260 may comprise a hardware processor, as well as digital memory, such as non-volatile memory (e.g., flash memory), both of which may be utilized to assist in the processing, caching, and storage of data. The data may include data a) captured from sensors (which may be, e.g., operatively coupled to the frame 230 or otherwise attached to the user 210), such as image capture devices (e.g., cameras in the inward-facing imaging system or the outward-facing imaging system), audio sensors (e.g., microphones), inertial measurement units (IMUs), accelerometers, compasses, global positioning system (GPS) units, radio devices, or gyroscopes; orb) acquired or processed using remote processing module 270 or remote data repository 280, possibly for passage to the display 220 after such processing or retrieval. The local processing and data module 260 may be operatively coupled by communication links 262 or 264, such as via wired or wireless communication links, to the remote processing module 270 or remote data repository 280 such that these remote modules are available as resources to the local processing and data module 260. In addition, remote processing module 280 and remote data repository 280 may be operatively coupled to each other.

In some embodiments, the remote processing module 270 may comprise one or more processors configured to analyze and process data or image information. In some embodiments, the remote data repository 280 may comprise a digital data storage facility, which may be available through the internet or other networking configuration in a "cloud" resource configuration. In some embodiments, all data is stored and all computations are performed in the local processing and data module, allowing fully autonomous use from a remote module.

Example Components of a Wearable System

Figure 3:
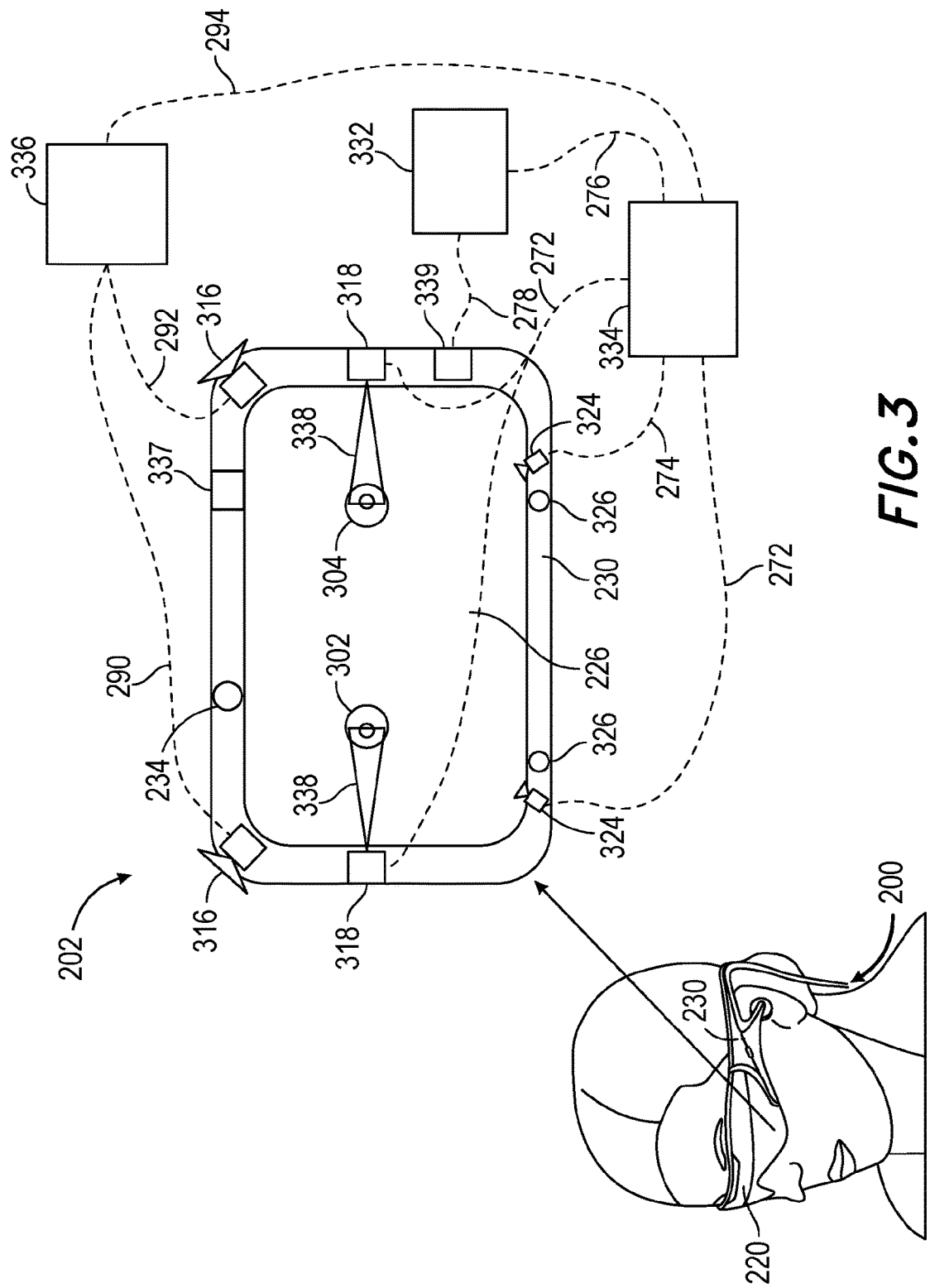
FIG. 3 schematically illustrates example components of a wearable system.

FIG. 3 schematically illustrates example components of a wearable system. FIG. 3 shows a wearable system 200 which can include a display 220 and a frame 230. A blown-up view 202 schematically illustrates various components of the wearable system 200. In certain implements, one or more of the components illustrated in FIG. 3 can be part of the display 220. The various components alone or in combination can collect a variety of data (such as e.g., audio, image, or video data) associated with the user of the wearable system 200 or the user's environment. It should be appreciated that other embodiments may have additional or fewer components depending on the application for which the wearable system is used. Nevertheless, FIG. 3 provides a basic idea of some of the various components and types of data that may be collected, analyzed, and stored through the wearable system.

FIG. 3 shows an example wearable system 200 which can include the display 220. The display 220 can comprise a display lens 226 that may be mounted to a user's head or a housing or frame 230, which corresponds to the frame 230. The display lens 226 may comprise one or more transparent mirrors positioned by the housing 230 in front of the user's eyes 302, 304 and may be configured to bounce projected light 338 into the eyes 302, 304 and facilitate beam shaping, while also allowing for transmission of at least some light from the local environment. The wavefront of the projected light beam 338 may be bent or focused to coincide with a desired focal distance of the projected light. As illustrated, two wide-field-of-view machine vision cameras 316 (also referred to as world cameras) can be coupled to the housing 230 to image the environment around the user. These cameras 316 can be dual capture visible light/non-visible (e.g., infrared) light cameras. The cameras 316 may be part of the outward-facing imaging system 464 shown in FIG. 4. Image acquired by the world cameras 316 can be processed by the pose processor 336. For example, the pose processor 336 can implement one or more object recognizers to identify a pose of a user or another person in the user's environment or to identify a physical object in the user's environment.

With continued reference to FIG. 3, a pair of scanned-laser shaped-wavefront (e.g., for depth) light projector modules with display mirrors and optics configured to project light 338 into the eyes 302, 304 are shown. The depicted view also shows two miniature infrared cameras 324 paired with infrared light sources 326 (such as light emitting diodes "LED"s), which are configured to be able to track the eyes 302, 304 of the user to support rendering and user input. The cameras 324 may be part of the inward-facing imaging system 462 shown in FIG. 4. The wearable system 200 can further feature a sensor assembly 339, which may comprise X, Y, and Z axis accelerometer capability as well as a magnetic compass and X, Y, and Z axis gyro capability, preferably providing data at a relatively high frequency, such as 200 Hz. The sensor assembly 339 may be part of the IMU described with reference to FIG. 2A The depicted system 200 can also comprise a head pose processor 336, such as an ASIC (application specific integrated circuit), FPGA (field programmable gate array), or ARM processor (advanced reduced-instruction-set machine), which may be configured to calculate real or near-real time user head pose from wide field of view image information output from the capture devices 316. The head pose processor 336 can be a hardware processor and can be implemented as part of the local processing and data module 260 shown in FIG. 2A.

The wearable system can also include one or more depth sensors 234. The depth sensor 234 can be configured to measure the distance between an object in an environment to a wearable device. The depth sensor 234 may include a laser scanner (e.g., a lidar), an ultrasonic depth sensor, or a depth sensing camera. In certain implementations, where the cameras 316 have depth sensing ability, the cameras 316 may also be considered as depth sensors 234.

Also shown is a processor 332 configured to execute digital or analog processing to derive pose from the gyro, compass, or accelerometer data from the sensor assembly 339. The processor 332 may be part of the local processing and data module 260 shown in FIG. 2. The wearable system 200 as shown in FIG. 3 can also include a position system such as, e.g., a GPS 337 (global positioning system) to assist with pose and positioning analyses. In addition, the GPS may further provide remotely-based (e.g., cloud-based) information about the user's environment. This information may be used for recognizing objects or information in user's environment.

The wearable system may combine data acquired by the GPS 337 and a remote computing system (such as, e.g., the remote processing module 270, another user's ARD, etc.) which can provide more information about the user's environment. As one example, the wearable system can determine the user's location based on GPS data and retrieve a world map (e.g., by communicating with a remote processing module 270) including virtual objects associated with the user's location. As another example, the wearable system 200 can monitor the environment using the world cameras 316 (which may be part of the outward-facing imaging system 464 shown in FIG. 4). Based on the images acquired by the world cameras 316, the wearable system 200 can detect objects in the environment. The wearable system can further use data acquired by the GPS 337 to interpret the characters.

The wearable system 200 may also comprise a rendering engine 334 which can be configured to provide rendering information that is local to the user to facilitate operation of the scanners and imaging into the eyes of the user, for the user's view of the world. The rendering engine 334 may be implemented by a hardware processor (such as, e.g., a central processing unit or a graphics processing unit). In some embodiments, the rendering engine is part of the local processing and data module 260. The rendering engine 334 can be communicatively coupled (e.g., via wired or wireless links) to other components of the wearable system 200. For example, the rendering engine 334, can be coupled to the eye cameras 324 via communication link 274, and be coupled to a projecting subsystem 318 (which can project light into user's eyes 302, 304 via a scanned laser arrangement in a manner similar to a retinal scanning display) via the communication link 272. The rendering engine 334 can also be in communication with other processing units such as, e.g., the sensor pose processor 332 and the image pose processor 336 via links 276 and 294 respectively.

The cameras 324 (e.g., mini infrared cameras) may be utilized to track the eye pose to support rendering and user input. Some example eye poses may include where the user is looking or at what depth he or she is focusing (which may be estimated with eye vergence). The GPS 337, gyros, compass, and accelerometers 339 may be utilized to provide coarse or fast pose estimates. One or more of the cameras 316 can acquire images and pose, which in conjunction with data from an associated cloud computing resource, may be utilized to map the local environment and share user views with others.

The example components depicted in FIG. 3 are for illustration purposes only. Multiple sensors and other functional modules are shown together for ease of illustration and description. Some embodiments may include only one or a subset of these sensors or modules. Further, the locations of these components are not limited to the positions depicted in FIG. 3. Some components may be mounted to or housed within other components, such as a belt-mounted component, a hand-held component, or a helmet component. As one example, the image pose processor 336, sensor pose processor 332, and rendering engine 334 may be positioned in a beltpack and configured to communicate with other components of the wearable system via wireless communication, such as ultra-wideband, Wi-Fi, Bluetooth, etc., or via wired communication. The depicted housing 230 preferably is head-mountable and wearable by the user. However, some components of the wearable system 200 may be worn to other portions of the user's body. For example, the speaker 240 may be inserted into the ears of a user to provide sound to the user.

Regarding the projection of light 338 into the eyes 302, 304 of the user, in some embodiment, the cameras 324 may be utilized to measure where the centers of a user's eyes are geometrically verged to, which, in general, coincides with a position of focus, or "depth of focus", of the eyes. A 3-dimensional surface of all points the eyes verge to can be referred to as the "horopter". The focal distance may take on a finite number of depths, or may be infinitely varying. Light projected from the vergence distance appears to be focused to the subject eye 302, 304, while light in front of or behind the vergence distance is blurred. Examples of wearable devices and other display systems of the present disclosure are also described in U.S. Patent Publication No. 2016/0270656, which is incorporated by reference herein in its entirety.

The human visual system is complicated and providing a realistic perception of depth is challenging. Viewers of an object may perceive the object as being three-dimensional due to a combination of vergence and accommodation. Vergence movements (e.g., rolling movements of the pupils toward or away from each other to converge the lines of sight of the eyes to fixate upon an object) of the two eyes relative to each other are closely associated with focusing (or "accommodation") of the lenses of the eyes. Under normal conditions, changing the focus of the lenses of the eyes, or accommodating the eyes, to change focus from one object to another object at a different distance will automatically cause a matching change in vergence to the same distance, under a relationship known as the "accommodation-vergence reflex." Likewise, a change in vergence will trigger a matching change in accommodation, under normal conditions. Display systems that provide a better match between accommodation and vergence may form more realistic and comfortable simulations of three-dimensional imagery.

Further spatially coherent light with a beam diameter of less than about 0.7 millimeters can be correctly resolved by the human eye regardless of where the eye focuses. Thus, to create an illusion of proper focal depth, the eye vergence may be tracked with the cameras 324, and the rendering engine 334 and projection subsystem 318 may be utilized to render all objects on or close to the horopter in focus, and all other objects at varying degrees of defocus (e.g., using intentionally-created blurring). Preferably, the system 220 renders to the user at a frame rate of about 60 frames per second or greater. As described above, preferably, the cameras 324 may be utilized for eye tracking, and software may be configured to pick up not only vergence geometry but also focus location cues to serve as user inputs. Preferably, such a display system is configured with brightness and contrast suitable for day or night use.

In some embodiments, the display system preferably has latency of less than about 20 milliseconds for visual object alignment, less than about 0.1 degree of angular alignment, and about 1 arc minute of resolution, which, without being limited by theory, is believed to be approximately the limit of the human eye. The display system 220 may be integrated with a localization system, which may involve GPS elements, optical tracking, compass, accelerometers, or other data sources, to assist with position and pose determination; localization information may be utilized to facilitate accurate rendering in the user's view of the pertinent world (e.g., such information would facilitate the glasses to know where they are with respect to the real world).

In some embodiments, the wearable system 200 is configured to display one or more virtual images based on the accommodation of the user's eyes. Unlike prior 3D display approaches that force the user to focus where the images are being projected, in some embodiments, the wearable system is configured to automatically vary the focus of projected virtual content to allow for a more comfortable viewing of one or more images presented to the user. For example, if the user's eyes have a current focus of 1 m, the image may be projected to coincide with the user's focus. If the user shifts focus to 3 m, the image is projected to coincide with the new focus. Thus, rather than forcing the user to a predetermined focus, the wearable system 200 of some embodiments allows the user's eye to a function in a more natural manner.

Such a wearable system 200 may eliminate or reduce the incidences of eye strain, headaches, and other physiological symptoms typically observed with respect to virtual reality devices. To achieve this, various embodiments of the wearable system 200 are configured to project virtual images at varying focal distances, through one or more variable focus elements (VFEs). In one or more embodiments, 3D perception may be achieved through a multi-plane focus system that projects images at fixed focal planes away from the user. Other embodiments employ variable plane focus, wherein the focal plane is moved back and forth in the z-direction to coincide with the user's present state of focus.

In both the multi-plane focus systems and variable plane focus systems, wearable system 200 may employ eye tracking to determine a vergence of the user's eyes, determine the user's current focus, and project the virtual image at the determined focus. In other embodiments, wearable system 200 comprises a light modulator that variably projects, through a fiber scanner, or other light generating source, light beams of varying focus in a raster pattern across the retina. Thus, the ability of the display of the wearable system 200 to project images at varying focal distances not only eases accommodation for the user to view objects in 3D, but may also be used to compensate for user ocular anomalies, as further described in U.S. Patent Publication No. 2016/0270656, which is incorporated by reference herein in its entirety. In some other embodiments, a spatial light modulator may project the images to the user through various optical components. For example, as described further below, the spatial light modulator may project the images onto one or more waveguides, which then transmit the images to the user.

Waveguide Stack Assembly

Figure 4:
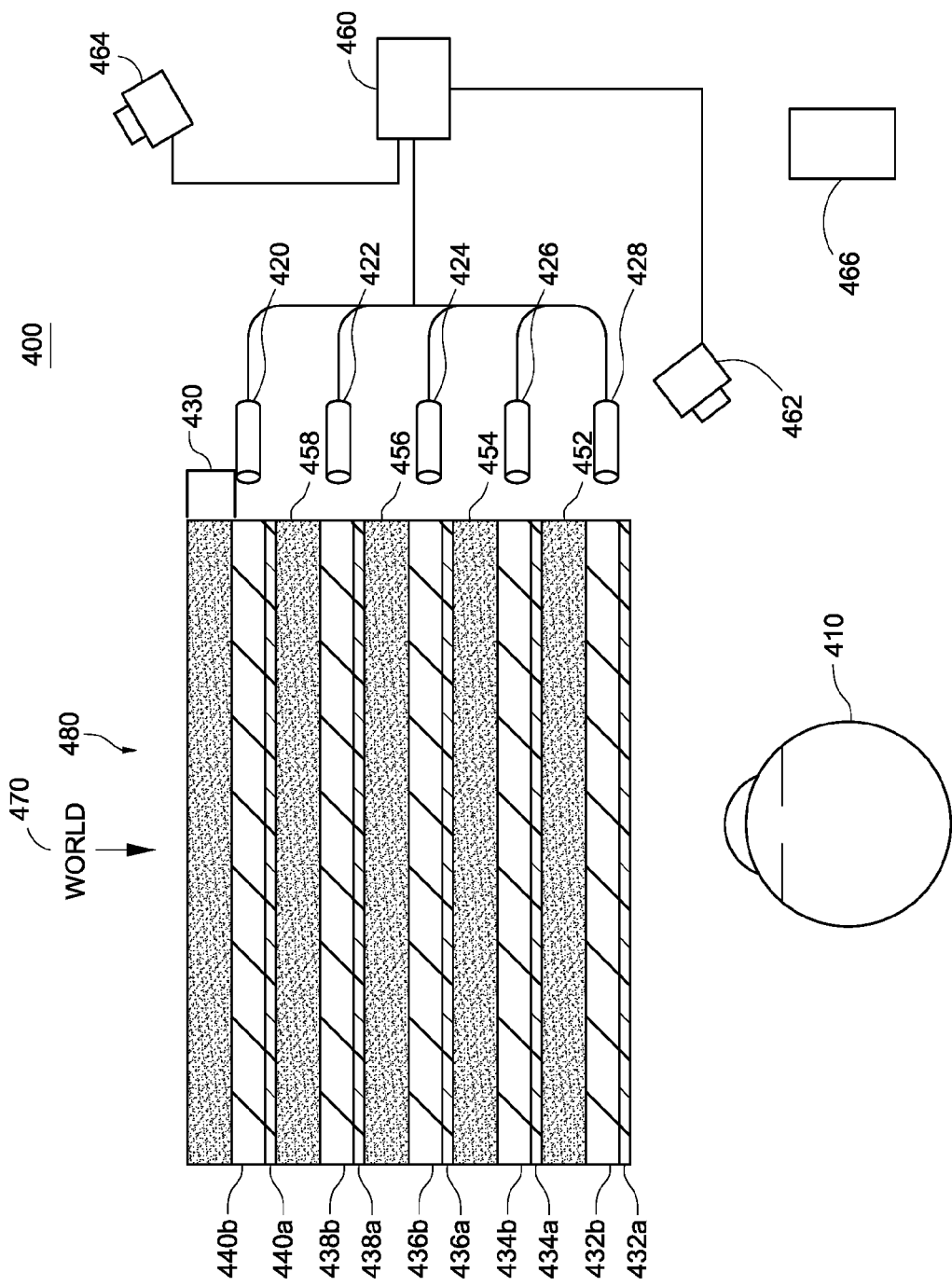
FIG. 4 schematically illustrates an example of a waveguide stack of a wearable device for outputting image information to a user.

FIG. 4 illustrates an example of a waveguide stack for outputting image information to a user. A wearable system 400 includes a stack of waveguides, or stacked waveguide assembly 480 that may be utilized to provide three-dimensional perception to the eye/brain using a plurality of waveguides 432b, 434b, 436b, 438b, 4400b. In some embodiments, the wearable system 400 may correspond to wearable system 200 of FIG. 2, with FIG. 4 schematically showing some parts of that wearable system 200 in greater detail. For example, in some embodiments, the waveguide assembly 480 may be integrated into the display 220 of FIG. 2.

With continued reference to FIG. 4, the waveguide assembly 480 may also include a plurality of features 458, 456, 454, 452 between the waveguides. In some embodiments, the features 458, 456, 454, 452 may be lenses. In other embodiments, the features 458, 456, 454, 452 may not be lenses. Rather, they may simply be spacers (e.g., cladding layers or structures for forming air gaps).

The waveguides 432b, 434b, 436b, 438b, 440b or the plurality of lenses 458, 456, 454, 452 may be configured to send image information to the eye with various levels of wavefront curvature or light ray divergence. Each waveguide level may be associated with a particular depth plane and may be configured to output image information corresponding to that depth plane. Image injection devices 420, 422, 424, 426, 428 may be utilized to inject image information into the waveguides 440b, 438b, 436b, 434b, 432b, each of which may be configured to distribute incoming light across each respective waveguide, for output toward the eye 410. Light exits an output surface of the image injection devices 420, 422, 424, 426, 428 and is injected into a corresponding input edge of the waveguides 440b, 438b, 436b, 434b, 432b. In some embodiments, a single beam of light (e.g., a collimated beam) may be injected into each waveguide to output an entire field of cloned collimated beams that are directed toward the eye 410 at particular angles (and amounts of divergence) corresponding to the depth plane associated with a particular waveguide.

In some embodiments, the image injection devices 420, 422, 424, 426, 428 are discrete displays that each produce image information for injection into a corresponding waveguide 440b, 438b, 436b, 434b, 432b, respectively. In some other embodiments, the image injection devices 420, 422, 424, 426, 428 are the output ends of a single multiplexed display which may, e.g., pipe image information via one or more optical conduits (such as fiber optic cables) to each of the image injection devices 420, 422, 424, 426, 428.

A controller 460 controls the operation of the stacked waveguide assembly 480 and the image injection devices 420, 422, 424, 426, 428. The controller 460 includes programming (e.g., instructions in a non-transitory computer-readable medium) that regulates the timing and provision of image information to the waveguides 440b, 438b, 436b, 434b, 432b. In some embodiments, the controller 460 may be a single integral device, or a distributed system connected by wired or wireless communication channels. The controller 460 may be part of the processing modules 260 or 270 (illustrated in FIG. 2) in some embodiments.

The waveguides 440b, 438b, 436b, 434b, 432b may be configured to propagate light within each respective waveguide by total internal reflection (TIR). The waveguides 440b, 438b, 436b, 434b, 432b may each be planar or have another shape (e.g., curved), with major top and bottom surfaces and edges extending between those major top and bottom surfaces. In the illustrated configuration, the waveguides 440b, 438b, 436b, 434b, 432b may each include light extracting optical elements 440a, 438a, 436a, 434a, 432a that are configured to extract light out of a waveguide by redirecting the light, propagating within each respective waveguide, out of the waveguide to output image information to the eye 410. Extracted light may also be referred to as outcoupled light, and light extracting optical elements may also be referred to as outcoupling optical elements. An extracted beam of light is outputted by the waveguide at locations at which the light propagating in the waveguide strikes a light redirecting element. The light extracting optical elements (440a, 438a, 436a, 434a, 432a) may, for example, be reflective or diffractive optical features. While illustrated disposed at the bottom major surfaces of the waveguides 440b, 438b, 436b, 434b, 432b for ease of description and drawing clarity, in some embodiments, the light extracting optical elements 440a, 438a, 436a, 434a, 432a may be disposed at the top or bottom major surfaces, or may be disposed directly in the volume of the waveguides 440b, 438b, 436b, 434b, 432b. In some embodiments, the light extracting optical elements 440a, 438a, 436a, 434a, 432a may be formed in a layer of material that is attached to a transparent substrate to form the waveguides 440b, 438b, 436b, 434b, 432b. In some other embodiments, the waveguides 440b, 438b, 436b, 434b, 432b may be a monolithic piece of material and the light extracting optical elements 440a, 438a, 436a, 434a, 432a may be formed on a surface or in the interior of that piece of material.

With continued reference to FIG. 4, as discussed herein, each waveguide 440b, 438b, 436b, 434b, 432b is configured to output light to form an image corresponding to a particular depth plane. For example, the waveguide 432b nearest the eye may be configured to deliver collimated light, as injected into such waveguide 432b, to the eye 410. The collimated light may be representative of the optical infinity focal plane. The next waveguide up 434b may be configured to send out collimated light which passes through the first lens 452 (e.g., a negative lens) before it can reach the eye 410. First lens 452 may be configured to create a slight convex wavefront curvature so that the eye/brain interprets light coming from that next waveguide up 434b as coming from a first focal plane closer inward toward the eye 410 from optical infinity. Similarly, the third up waveguide 436b passes its output light through both the first lens 452 and second lens 454 before reaching the eye 410. The combined optical power of the first and second lenses 452 and 454 may be configured to create another incremental amount of wavefront curvature so that the eye/brain interprets light coming from the third waveguide 436b as coming from a second focal plane that is even closer inward toward the person from optical infinity than was light from the next waveguide up 434b.

The other waveguide layers (e.g., waveguides 438b, 440b) and lenses (e.g., lenses 456, 458) are similarly configured, with the highest waveguide 440b in the stack sending its output through all of the lenses between it and the eye for an aggregate focal power representative of the closest focal plane to the person. To compensate for the stack of lenses 458, 456, 454, 452 when viewing/interpreting light coming from the world 470 on the other side of the stacked waveguide assembly 480, a compensating lens layer 430 may be disposed at the top of the stack to compensate for the aggregate power of the lens stack 458, 456, 454, 452 below. (Compensating lens layer 430 and the stacked waveguide assembly 480 as a whole may be configured such that light coming from the world 470 is conveyed to the eye 410 at substantially the same level of divergence (or collimation) as the light had when it was initially received by the stacked waveguide assembly 480.) Such a configuration provides as many perceived focal planes as there are available waveguide/lens pairings. Both the light extracting optical elements of the waveguides and the focusing aspects of the lenses may be static (e.g., not dynamic or electro-active). In some alternative embodiments, either or both may be dynamic using electro-active features.

With continued reference to FIG. 4, the light extracting optical elements 440*a*, 438*a*, 436*a*, 434*a*, 432*a* may be configured to both redirect light out of their respective waveguides and to output this light with the appropriate amount of divergence or collimation for a particular depth plane associated with the waveguide. As a result, waveguides having different associated depth planes may have different configurations of light extracting optical elements, which output light with a different amount of divergence depending on the associated depth plane. In some embodiments, as discussed herein, the light extracting optical elements 440*a*, 438*a*, 436*a*, 434*a*, 432*a* may be volumetric or surface features, which may be configured to output light at specific angles. For example, the light extracting optical elements 440*a*, 438*a*, 436*a*, 434*a*, 432*a* may be volume holograms, surface holograms, and/or diffraction gratings. Light extracting optical elements, such as diffraction gratings, are described in U.S. Patent Publication No. 2015/0178939, published Jun. 25, 2015, which is incorporated by reference herein in its entirety.

In some embodiments, the light extracting optical elements 440*a*, 438*a*, 436*a*, 434*a*, 432*a* are diffractive features that form a diffraction pattern, or "diffractive optical element" (also referred to herein as a "DOE"). Preferably, the DOE has a relatively low diffraction efficiency so that only a portion of the light of the beam is deflected away toward the eye 410 with each intersection of the DOE, while the rest continues to move through a waveguide via total internal reflection. The light carrying the image information can thus be divided into a number of related exit beams that exit the waveguide at a multiplicity of locations and the result is a fairly uniform pattern of exit emission toward the eye 304 for this particular collimated beam bouncing around within a waveguide.

In some embodiments, one or more DOEs may be switchable between "on" state in which they actively diffract, and "off" state in which they do not significantly diffract. For instance, a switchable DOE may comprise a layer of polymer dispersed liquid crystal, in which microdroplets comprise a diffraction pattern in a host medium, and the refractive index of the microdroplets can be switched to substantially match the refractive index of the host material (in which case the pattern does not appreciably diffract incident light) or the microdroplet can be switched to an index that does not match that of the host medium (in which case the pattern actively diffracts incident light).

In some embodiments, the number and distribution of depth planes or depth of field may be varied dynamically based on the pupil sizes or orientations of the eyes of the viewer. Depth of field may change inversely with a viewer's pupil size. As a result, as the sizes of the pupils of the viewer's eyes decrease, the depth of field increases such that one plane that is not discernible because the location of that plane is beyond the depth of focus of the eye may become discernible and appear more in focus with reduction of pupil size and commensurate with the increase in depth of field. Likewise, the number of spaced apart depth planes used to present different images to the viewer may be decreased with the decreased pupil size. For example, a viewer may not be able to clearly perceive the details of both a first depth plane and a second depth plane at one pupil size without adjusting the accommodation of the eye away from one depth plane and to the other depth plane. These two depth planes may, however, be sufficiently in focus at the same time to the user at another pupil size without changing accommodation.

In some embodiments, the display system may vary the number of waveguides receiving image information based upon determinations of pupil size or orientation, or upon receiving electrical signals indicative of particular pupil size or orientation. For example, if the user's eyes are unable to distinguish between two depth planes associated with two waveguides, then the controller 460 (which may be an embodiment of the local processing and data module 260) can be configured or programmed to cease providing image information to one of these waveguides. Advantageously, this may reduce the processing burden on the system, thereby increasing the responsiveness of the system. In embodiments in which the DOEs for a waveguide are switchable between the on and off states, the DOEs may be switched to the off state when the waveguide does receive image information.

In some embodiments, it may be desirable to have an exit beam meet the condition of having a diameter that is less than the diameter of the eye of a viewer. However, meeting this condition may be challenging in view of the variability in size of the viewer's pupils. In some embodiments, this condition is met over a wide range of pupil sizes by varying the size of the exit beam in response to determinations of the size of the viewer's pupil. For example, as the pupil size decreases, the size of the exit beam may also decrease. In some embodiments, the exit beam size may be varied using a variable aperture.

The wearable system 400 can include an outward-facing imaging system 464 (e.g., a digital camera) that images a portion of the world 470. This portion of the world 470 may be referred to as the field of view (FOV) of a world camera and the imaging system 464 is sometimes referred to as an FOV camera. The FOV of the world camera may or may not be the same as the FOV of a viewer 210 which encompasses a portion of the world 470 the viewer 210 perceives at a given time. For example, in some situations, the FOV of the world camera may be larger than the viewer 210 of the viewer 210 of the wearable system 400. The entire region available for viewing or imaging by a viewer may be referred to as the field of regard (FOR). The FOR may include 4π steradians of solid angle surrounding the wearable system 400 because the wearer can move his body, head, or eyes to perceive substantially any direction in space. In other contexts, the wearer's movements may be more constricted, and accordingly the wearer's FOR may subtend a smaller solid angle. Images obtained from the outward-facing imaging system 464 can be used to track gestures made by the user (e.g., hand or finger gestures), detect objects in the world 470 in front of the user, and so forth.

The wearable system 400 can include an audio sensor 232, e.g., a microphone, to capture ambient sound. As described above, in some embodiments, one or more other audio sensors can be positioned to provide stereo sound reception useful to the determination of location of a speech source. The audio sensor 232 can comprise a directional microphone, as another example, which can also provide such useful directional information as to where the audio source is located. The wearable system 400 can use information from both the outward-facing imaging system 464 and the audio sensor 230 in locating a source of speech, or to determine an active speaker at a particular moment in time, etc. For example, the wearable system 400 can use the voice recognition alone or in combination with a reflected image of the speaker (e.g., as seen in a mirror) to determine the identity of the speaker. As another example, the wearable system 400 can determine a position of the speaker in an environment based on sound acquired from directional microphones. The wearable system 400 can parse the sound coming from the speaker's position with speech recognition algorithms to determine the content of the speech and use voice recognition techniques to determine the identity (e.g., name or other demographic information) of the speaker.

The wearable system 400 can also include an inward-facing imaging system 466 (e.g., a digital camera), which observes the movements of the user, such as the eye movements and the facial movements. The inward-facing imaging system 466 may be used to capture images of the eye 410 to determine the size and/or orientation of the pupil of the eye 304. The inward-facing imaging system 466 can be used to obtain images for use in determining the direction the user is looking (e.g., eye pose) or for biometric identification of the user (e.g., via iris identification). In some embodiments, at least one camera may be utilized for each eye, to separately determine the pupil size or eye pose of each eye independently, thereby allowing the presentation of image information to each eye to be dynamically tailored to that eye. In some other embodiments, the pupil diameter or orientation of only a single eye 410 (e.g., using only a single camera per pair of eyes) is determined and assumed to be similar for both eyes of the user. The images obtained by the inward-facing imaging system 466 may be analyzed to determine the user's eye pose or mood, which can be used by the wearable system 400 to decide which audio or visual content should be presented to the user. The wearable system 400 may also determine head pose (e.g., head position or head orientation) using sensors such as IMUs, accelerometers, gyroscopes, etc.

The wearable system 400 can include a user input device 466 by which the user can input commands to the controller 460 to interact with the wearable system 400. For example, the user input device 466 can include a trackpad, a touchscreen, a joystick, a multiple degree-of-freedom (DOF) controller, a capacitive sensing device, a game controller, a keyboard, a mouse, a directional pad (D-pad), a wand, a haptic device, a totem (e.g., functioning as a virtual user input device), and so forth. A multi-DOF controller can sense user input in some or all possible translations (e.g., left/right, forward/backward, or up/down) or rotations (e.g., yaw, pitch, or roll) of the controller. A multi-DOF controller which supports the translation movements may be referred to as a 3DOF while a multi-DOF controller which supports the translations and rotations may be referred to as 6DOF. In some cases, the user may use a finger (e.g., a thumb) to press or swipe on a touch-sensitive input device to provide input to the wearable system 400 (e.g., to provide user input to a user interface provided by the wearable system 400). The user input device 466 may be held by the user's hand during the use of the wearable system 400. The user input device 466 can be in wired or wireless communication with the wearable system 400.

Other Components of the Wearable System

In many implementations, the wearable system may include other components in addition or in alternative to the components of the wearable system described above. The wearable system may, for example, include one or more haptic devices or components. The haptic devices or components may be operable to provide a tactile sensation to a user. For example, the haptic devices or components may provide a tactile sensation of pressure or texture when touching virtual content (e.g., virtual objects, virtual tools, other virtual constructs). The tactile sensation may replicate a feel of a physical object which a virtual object represents, or may replicate a feel of an imagined object or character (e.g., a dragon) which the virtual content represents. In some implementations, haptic devices or components may be worn by the user (e.g., a user wearable glove). In some implementations, haptic devices or components may be held by the user.

The wearable system may, for example, include one or more physical objects which are manipulable by the user to allow input or interaction with the wearable system. These physical objects may be referred to herein as totems. Some totems may take the form of inanimate objects, such as for example, a piece of metal or plastic, a wall, a surface of table. In certain implementations, the totems may not actually have any physical input structures (e.g., keys, triggers, joystick, trackball, rocker switch). Instead, the totem may simply provide a physical surface, and the wearable system may render a user interface so as to appear to a user to be on one or more surfaces of the totem. For example, the wearable system may render an image of a computer keyboard and trackpad to appear to reside on one or more surfaces of a totem. For example, the wearable system may render a virtual computer keyboard and virtual trackpad to appear on a surface of a thin rectangular plate of aluminum which serves as a totem. The rectangular plate does not itself have any physical keys or trackpad or sensors. However, the wearable system may detect user manipulation or interaction or touches with the rectangular plate as selections or inputs made via the virtual keyboard or virtual trackpad. The user input device 466 (shown in FIG. 4) may be an embodiment of a totem, which may include a trackpad, a touchpad, a trigger, a joystick, a trackball, a rocker or virtual switch, a mouse, a keyboard, a multi-degree-of-freedom controller, or another physical input device. A user may use the totem, alone or in combination with poses, to interact with the wearable system or other users.

Examples of haptic devices and totems usable with the wearable devices, HMD, and display systems of the present disclosure are described in U.S. Patent Publication No. 2015/0016777, which is incorporated by reference herein in its entirety.

Example of an Eye Image

Figure 5:
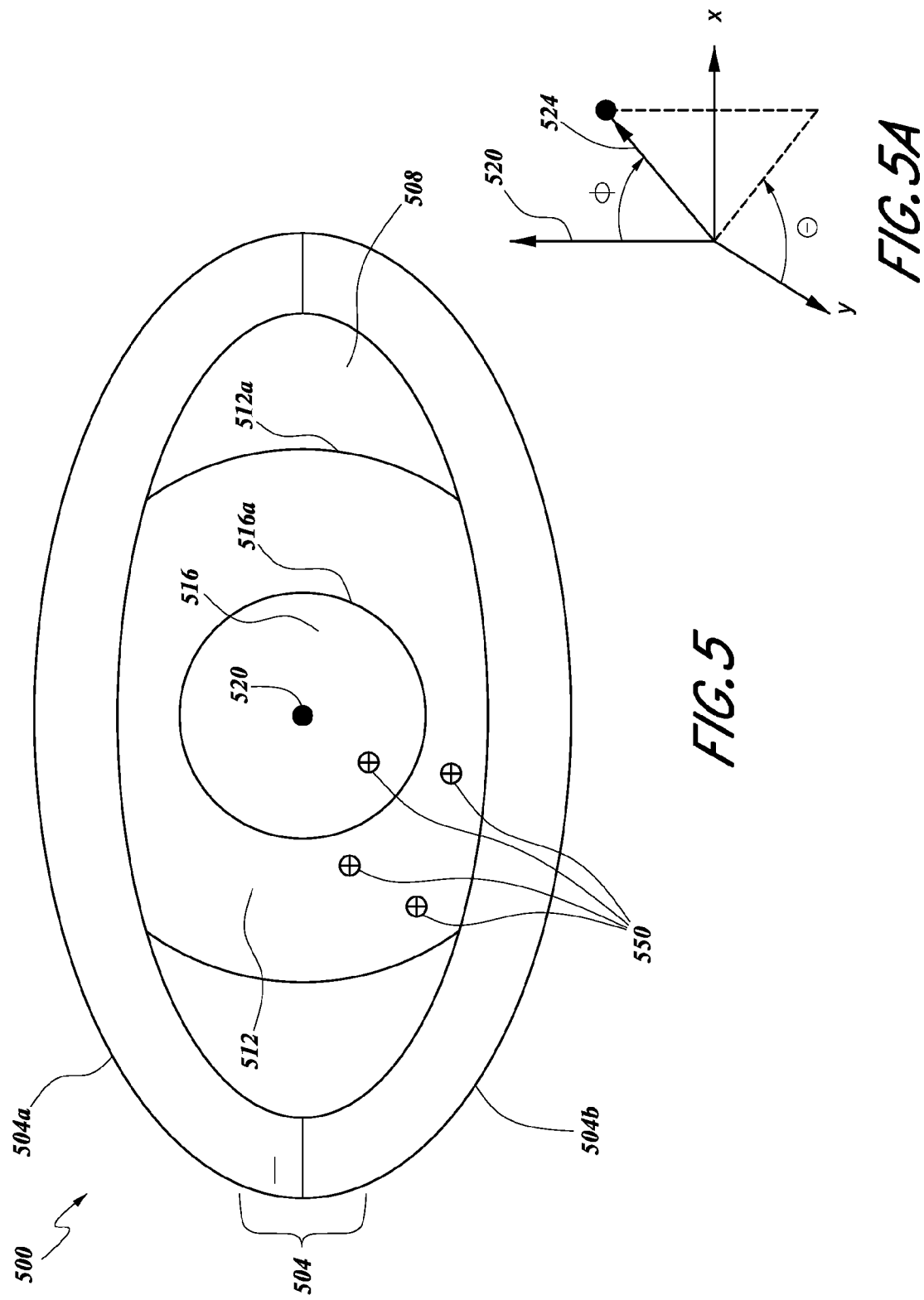
FIG. 5 schematically illustrates an example of an eye.

FIG. 5 illustrates an image of an eye 500 with eyelids 504, sclera 508 (the "white" of the eye), iris 512, and pupil 516. Curve 516a shows the pupillary boundary between the pupil 516 and the iris 512, and curve 512a shows the limbic boundary between the iris 512 and the sclera 508. The eyelids 504 include an upper eyelid 504a and a lower eyelid 504b. The eye 500 is illustrated in a natural resting pose (e.g., in which the user's face and gaze are both oriented as they would be toward a distant object directly ahead of the user). The natural resting pose of the eye 500 can be indicated by a natural resting direction 520, which is a direction orthogonal to the surface of the eye 500 when in the natural resting pose (e.g., directly out of the plane for the eye 500 shown in FIG. 5) and in this example, centered within the pupil 516.

As the eye 500 moves to look toward different objects, the eye pose will change relative to the natural resting direction 520. The current eye pose can be determined with reference to an eye pose direction 524, which is a direction orthogonal to the surface of the eye (and centered in within the pupil 516) but oriented toward the object at which the eye is currently directed. With reference to an example coordinate system shown in FIG. 5A, the pose of the eye 500 can be expressed as two angular parameters indicating an azimuthal deflection and a zenithal deflection of the eye pose direction 524 of the eye, both relative to the natural resting direction 520 of the eye. For purposes of illustration, these angular parameters can be represented as θ (azimuthal deflection, determined from a fiducial azimuth) and φ (zenithal deflection, sometimes also referred to as a polar deflection). In some implementations, angular roll of the eye around the eye pose direction 524 can be included in the determination of eye pose, and angular roll can be included in the following analysis. In other implementations, other techniques for determining the eye pose can be used, for example, a pitch, yaw, and optionally roll system.

The light sources 326 can illuminate the eye 500 (e.g., in the IR), and reflections of the light sources from the eye (typically off of the cornea) are referred to as glints. FIG. 5 schematically shows an example where there are four glints 550. The positions, number, brightnesses, etc. of the glints 550 can depend on the position and number of the light sources 326, the pose of the eye, and so forth. An eye-tracking camera 324 can obtain eye images, and a processor can analyze the eye images to determine positions and movements of the glints for eye-tracking.

An eye image can be obtained from a video using any appropriate process, for example, using a video processing algorithm that can extract an image from one or more sequential frames (or non-sequential frames). The inward-facing imaging system 462 of FIG. 4 or the camera 324 and light source 326 of FIG. 3 can be utilized to provide the video or image(s) of one or both of the eyes. The pose of the eye can be determined from the eye image using a variety of eye-tracking techniques. For example, an eye pose can be determined by considering the lensing effects of the cornea on light sources that are provided. Any suitable eye tracking technique can be used for determining eye pose in the eyelid shape estimation techniques described herein.

Example of an Eye Tracking System

Figure 6:
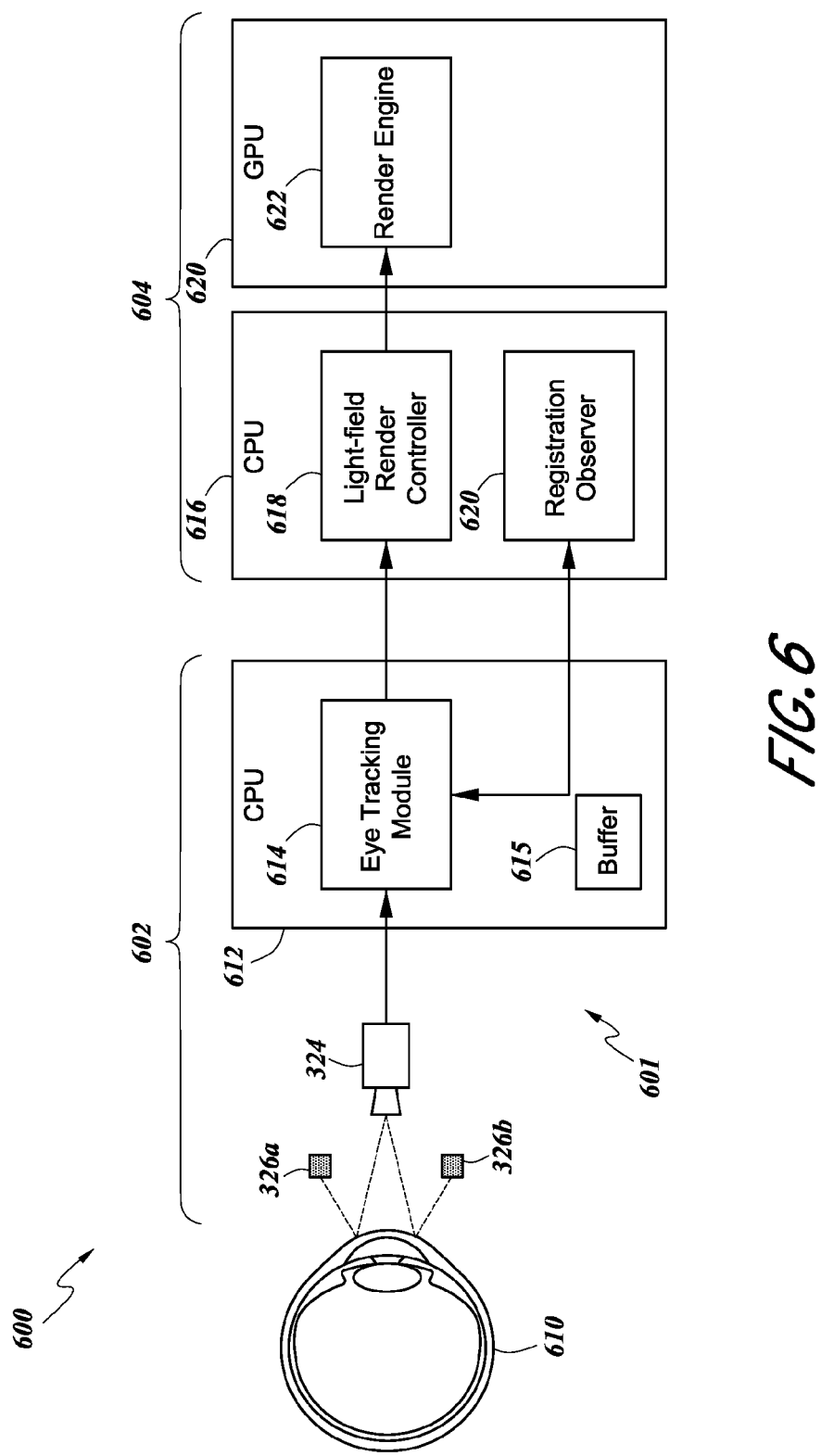
FIG. 6 is a schematic diagram of a wearable system that includes an eye tracking system.

FIG. 6 illustrates a schematic diagram of a wearable system 600 that includes an eye tracking system. The wearable system 600 may, in at least some embodiments, include components located in a head-mounted unit 602 and components located in a non-head-mounted unit 604. Non-head mounted unit 604 may be, as examples, a belt-mounted component, a hand-held component, a component in a backpack, a remote component, etc. Incorporating some of the components of the wearable system 600 in non-head-mounted unit 604 may help to reduce the size, weight, complexity, and cost of the head-mounted unit 602. In some implementations, some or all of the functionality described as being performed by one or more components of head-mounted unit 602 and/or non-head mounted 604 may be provided by way of one or more components included elsewhere in the wearable system 600. For example, some or all of the functionality described below in association with a CPU 612 of head-mounted unit 602 may be provided by way of a CPU 616 of non-head mounted unit 604, and vice versa. In some examples, some or all of such functionality may be provided by way of peripheral devices of wearable system 600. Furthermore, in some implementations, some or all of such functionality may be provided by way of one or more cloud computing devices or other remotely-located computing devices in a manner similar to that which has been described above with reference to FIG. 2.

As shown in FIG. 6, wearable system 600 can include an eye tracking system 601 including a camera 324 that captures images of a user's eye 610. If desired, the eye tracking system may also include light sources 326a and 326b (such as light emitting diodes "LED"s). The light sources 326a and 326b may generate glints (e.g., reflections off of the user's eyes that appear in images of the eye captured by camera 324). The positions of the light sources 326a and 326b relative to the camera 324 may be known and, as a consequence, the positions of the glints within images captured by camera 324 may be used in tracking the user's eyes. In at least one embodiment, there may be one light source 326 and one camera 324 associated with a single one of the user's eyes 610. In another embodiment, there may be one light source 326 and one camera 324 associated with each of a user's eyes. 610. In yet other embodiments, there may be one or more cameras 324 and one or more light sources 326 associated with one or each of a user's eyes 610. As a specific example, there may be two light sources 326a and 326b and one or more cameras 324 associated with each of a user's eyes 610. As another example, there may be three or more light sources such as light sources 326a and 326b and one or more cameras 324 associated with each of a user's eyes 610.

Eye tracking module 614 may receive images from eye tracking camera(s) 324 and may analyze the images to extract various pieces of information. As examples, the eye tracking module 614 may detect the user's eye poses, a three-dimensional position of the user's eye relative to the eye tracking camera 324 (and to the head-mounted unit 602), the direction one or both of the user's eyes 610 are focused on, the user's vergence depth (e.g., the depth from the user at which the user is focusing on), the positions of the user's pupils, the positions of the user's cornea and cornea sphere, the center of rotation of each of the user's eyes, and the center of perspective of each of the user's eyes. As shown in FIG. 6, eye tracking module 614 may be a software module implemented using a CPU 612 in a head-mounted unit 602.

Data from eye tracking module 614 may be provided to other components in the wearable system. As example, such data may be transmitted to components in a non-head-mounted unit 604 such as CPU 616 including software modules for a light-field render controller 618 and a registration observer 620.

Render controller 618 may use information from eye tracking module 614 to adjust images displayed to the user by render engine 622 (e.g., a render engine that may be a software module in GPU 620 and that may provide images to display 220). As an example, the render controller 618 may adjust images displayed to the user based on the user's center of rotation or center of perspective. In particular, the render controller 618 may use information on the user's center of perspective to simulate a render camera (e.g., to simulate collecting images from the user's perspective) and may adjust images displayed to the user based on the simulated render camera.

A "render camera," which is sometimes also referred to as a "pinhole perspective camera" (or simply "perspective camera") or "virtual pinhole camera" (or simply "virtual camera"), is a simulated camera for use in rendering virtual image content possibly from a database of objects in a virtual world. The objects may have locations and orientations relative to the user or wearer and possibly relative to real objects in the environment surrounding the user or wearer. In other words, the render camera may represent a perspective within render space from which the user or wearer is to view 3D virtual contents of the render space (e.g., virtual objects). The render camera may be managed by a render engine to render virtual images based on the database of virtual objects to be presented to said eye. The virtual images may be rendered as if taken from the perspective the user or wearer. For example, the virtual images may be rendered as if captured by a pinhole camera (corresponding to the "render camera") having a specific set of intrinsic parameters (e.g., focal length, camera pixel size, principal point coordinates, skew/distortion parameters, etc.), and a specific set of extrinsic parameters (e.g., translational components and rotational components relative to the virtual world). The virtual images are taken from the perspective of such a camera having a position and orientation of the render camera (e.g., extrinsic parameters of the render camera). It follows that the system may define and/or adjust intrinsic and extrinsic render camera parameters. For example, the system may define a particular set of extrinsic render camera parameters such that virtual images may be rendered as if captured from the perspective of a camera having a specific location with respect to the user's or wearer's eye so as to provide images that appear to be from the perspective of the user or wearer. The system may later dynamically adjust extrinsic render camera parameters on-the-fly so as to maintain registration with said specific location. Similarly, intrinsic render camera parameters may be defined and dynamically adjusted over time. In some implementations, the images are rendered as if captured from the perspective of a camera having an aperture (e.g., pinhole) at a specific location with respect to the user's or wearer's eye (such as the center of perspective or center of rotation, or elsewhere).

In some embodiments, the system may create or dynamically reposition and/or reorient one render camera for the user's left eye, and another render camera for the user's right eye, as the user's eyes are physically separated from one another and thus consistently positioned at different locations. It follows that, in at least some implementations, virtual content rendered from the perspective of a render camera associated with the viewer's left eye may be presented to the user through an eyepiece on the left side of a head-mounted display (e.g., head-mounted unit 602), and that virtual content rendered from the perspective of a render camera associated with the user's right eye may be presented to the user through an eyepiece on the right side of such a head-mounted display. Further details discussing the creation, adjustment, and use of render cameras in rendering processes are provided in U.S. Pat. No. 10,559,127, entitled "METHODS AND SYSTEMS FOR DETECTING AND COMBINING STRUCTURAL FEATURES IN 3D RECONSTRUCTION," which is expressly incorporated herein by reference in its entirety for all purposes.

In some examples, one or more modules (or components) of the system 600 (e.g., light-field render controller 618, render engine 620, etc.) may determine the position and orientation of the render camera within render space based on the position and orientation of the user's head and eyes (e.g., as determined based on head pose and eye tracking data, respectively). That is, the system 600 may effectively map the position and orientation of the user's head and eyes to particular locations and angular positions within a 3D virtual environment, place and orient render cameras at the particular locations and angular positions within the 3D virtual environment, and render virtual content for the user as it would be captured by the render camera. Further details discussing real world to virtual world mapping processes are provided in U.S. Pat. No. 10,521,025, entitled "SELECTING VIRTUAL OBJECTS IN A THREE-DIMENSIONAL SPACE," which is expressly incorporated herein by reference in its entirety for all purposes. As an example, the render controller 618 may adjust the depths at which images are displayed by selecting which depth plane (or depth planes) are utilized at any given time to display the images. In some implementations, such a depth plane switch may be carried out through an adjustment of one or more intrinsic render camera parameters. For example, the light-field render controller 618 may adjust the focal lengths of render cameras when executing a depth plane switch or adjustment. Depth planes may be switched based on the user's determined vergence or fixation depth.

Registration observer 620 may use information from eye tracking module 614 to identify whether the head-mounted unit 602 is properly positioned on a user's head. As an example, the eye tracking module 614 may provide eye location information, such as the positions of the centers of rotation of the user's eyes, indicative of the three-dimensional position of the user's eyes relative to camera 324 and head-mounted unit 602 and the eye tracking module 614 may use the location information to determine if display 220 is properly aligned in the user's field of view, or if the head-mounted unit 602 (or headset) has slipped or is otherwise misaligned with the user's eyes. As examples, the registration observer 620 may be able to determine if the head-mounted unit 602 has slipped down the user's nose bridge, thus moving display 220 away and down from the user's eyes (which may be undesirable), if the head-mounted unit 602 has been moved up the user's nose bridge, thus moving display 220 closer and up from the user's eyes, if the head-mounted unit 602 has been shifted left or right relative the user's nose bridge, if the head-mounted unit 602 has been lifted above the user's nose bridge, or if the head-mounted unit 602 has been moved in these or other ways away from a desired position or range of positions. In general, registration observer 620 may be able to determine if head-mounted unit 602, in general, and displays 220, in particular, are properly positioned in front of the user's eyes. In other words, the registration observer 620 may determine if a left display in display system 220 is appropriately aligned with the user's left eye and a right display in display system 220 is appropriately aligned with the user's right eye. The registration observer 620 may determine if the head-mounted unit 602 is properly positioned by determining if the head-mounted unit 602 is positioned and oriented within a desired range of positions and/or orientations relative to the user's eyes.

In at least some embodiments, registration observer 620 may generate user feedback in the form of alerts, messages, or other content. Such feedback may be provided to the user to inform the user of any misalignment of the head-mounted unit 602, along with optional feedback on how to correct the misalignment (such as a suggestion to adjust the head-mounted unit 602 in a particular manner).

Example registration observation and feedback techniques, which may be utilized by registration observer 620, are described in U.S. Pat. No. 10,473,042, entitled "PERIOCULAR TEST FOR MIXED REALITY CALIBRATION" and U.S. Patent Publication No. 2019/0222830, entitled "DISPLAY SYSTEMS AND METHODS FOR DETERMINING REGISTRATION BETWEEN A DISPLAY AND A USER'S EYES," both of which are incorporated by reference herein in their entirety.

Eye Tracking Using Alternate Sampling

One or more eye tracking cameras, such as camera(s) 324, can capture video (including, for instance, frames of a video) and/or image(s) (sometimes referred to as visual data or gaze vector(s)) of a left eye and right eye at a particular frame rate. The frame rate can be indicative of the exposure time of an eye during the video capture. For example, a higher frame rate can be indicative of a longer exposure time, which may lead to detecting more events as described herein. FIG. 7A illustrates a graph 700A of capturing visual data of the left eye and right eye at a frame rate (sometimes referred to as a sampling rate or sample rate) of 30 frames per second (fps) (or a sampling rate of 30 Hz). The x-axis of the graph 700A represents time. Top bars illustrate captured visual data of the left eye labeled L1, L2, L3, and L4 (corresponding to visual data captured at time instances (or times) t1, t2, t3, and t4). The time instances at which visual data is captured (or sampled) can be sometimes referred to as sampling intervals or sampling times. Bottom bars illustrate captured visual data of the right eye labeled R1, R2, R3, and R4 (corresponding to visual data captured at time instances t1, t2, t3, and t4). As illustrated, visual data from the left and right eye are generally captured at the same times. In FIG. 7A, the time between successive visual data samples of the left eye is 33.3 milliseconds (ms) (corresponding to 1/30 Hz). Similarly, the time between successive visual data samples of the right eye is 33.3 milliseconds (ms) (corresponding to 1/30 Hz). In some variations, one or more cameras can capture video of the left and right eye at different sampling rates.

FIG. 7B illustrates a graph 700B of capturing visual data of the left eye and right eye at frame rate of 60 frames per second (fps) (or sampling rate of 60 Hz). The graph 700B is similar to the graph 700A, except that more visual data is illustrated as being captured in FIG. 7B due to the higher sampling rate. In particular, the graph 700B illustrates captured visual data L1 to L7 of the left eye and visual data R1 to R7 of the right eye (corresponding to time instances t1 to t7). Visual data from the left and right eye are generally captured at the same times. In FIG. 7B, the time between successive visual data samples of the left eye is 16.7 (ms) (corresponding to 1/60 Hz). Similarly, the time between successive visual data samples of the right eye is 16.7 (ms) (corresponding to 1/60 Hz). As shown in the graph 700B, one of the advantages of using a higher sampling rate is the ability to detect events (such as, changes in the eye movement or eye pose) with faster rate of occurrence. For instance, in the graph 700B, the shortest detectable event duration is 16.7 ms, while in the graph 700A, the shortest detectable event duration is about 33.3 ms. Another advantage of using a higher sampling rate is the decrease in sampling latency, which can correspond to the time duration between successive visual data samples. Sampling latency can be indicative of the time duration for storing a new visual data sample in a memory buffer that stores captured visual data. Lower sampling latency may be preferable for detecting rapid events, such as saccadic eye movements (which can correspond to rapid movements of the eye when changing fixation). Sampling rates illustrated in FIGS. 7A and 7B are merely examples and other higher or lower sampling rates can be used (such as, 40 Hz, 60 Hz, 100 Hz, 120 Hz, or the like).

While using higher sampling rates can be beneficial for improved detection of events, increasing the sampling rate can cause an increase in power consumption, an increase in computing speed, an increase in usage of computing resources, etc. Additionally or alternatively, availability of one or more eye tracking cameras supporting higher sampling rates can be more limited that for lower sampling rates. As a result, eye tracking at higher sampling rates may be costlier and harder to implement in a wearable system.

Figure 8:
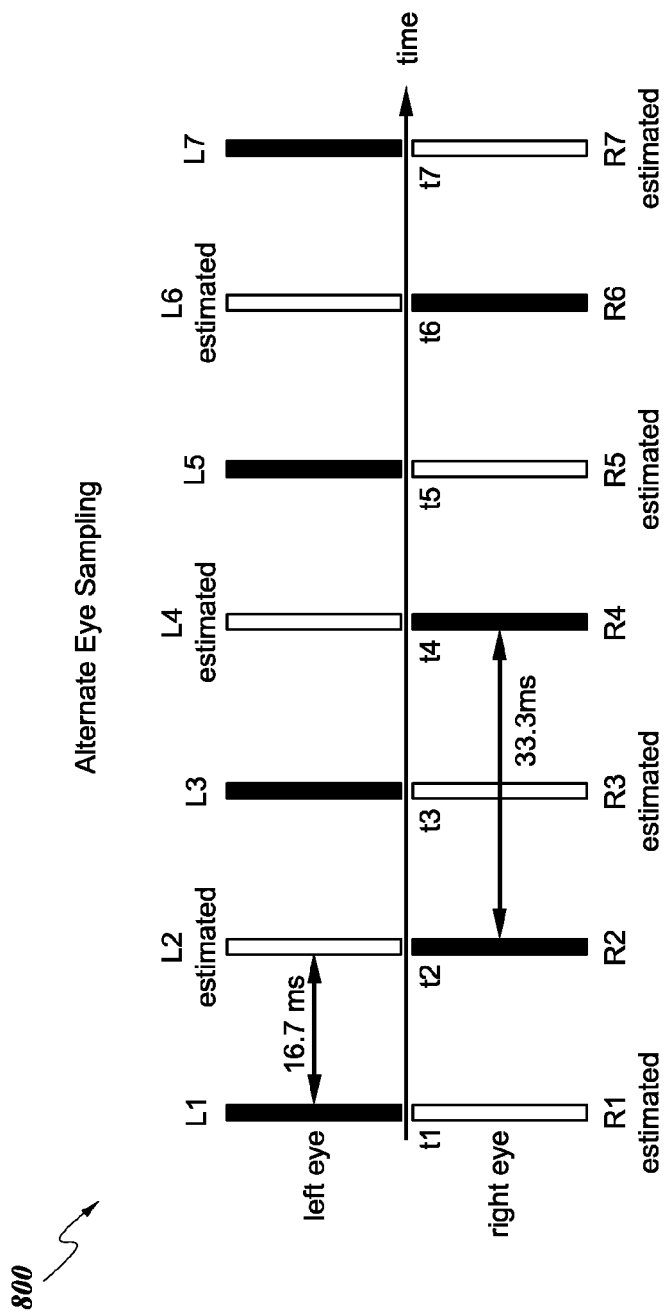
FIG. 8 is a graph that illustrates capturing visual data of a left eye and a right eye using alternate sampling.

To obtain the benefits associated with utilizing a higher sampling rate while retaining the simplicity associated with using lower sampling rates, alternate sampling can be implemented. FIG. 8 is a graph 800 illustrating capturing visual data of a left eye and a right eye using alternate sampling. Similar to the graphs 700A and 700B, in the graph 800 top bars represent captured visual data of the left eye, and bottom bars represent captured visual data of the right eye. As illustrated in FIG. 8, one or more eye tracking cameras for the left and right eyes can be configured to alternate capture of the visual data of each eye. For example, as illustrated, the visual data for the left eye (L1) is captured at an initial time (such as, t1) while during this initial time, the visual data for the right eye is not captured. At the next time (e.g., t2), the visual data for the right eye (R2) is captured, but the visual data for the left eye is not captured. In some implementations, while visual data for the right eye is not captured during t1, an estimate of the visual data for the right eye may be provided at time t1 instead. Similarly, while visual data for the left eye is not captured during t2, an estimate of the visual data for the left eye may be provided at time t2 instead. This process can continue for the subsequent time instances t3, t4, t5, t6, t7, and so on.

As a result, one or more eye tracking cameras for each of the eyes alternate the capture of the visual data. Dark bars in the graph 800 represent the visual data actually captured by one or more eye tracking cameras for the left and right eyes. As described below, light bars in the graph 800 represent estimated visual data for the left and right eyes. While capture of the visual data of the left eye is illustrated as being performed at the initial time, capture of the visual data of the right eye may be performed instead.

In FIG. 8, one or more eye tracking cameras of the left eye are illustrated as capturing the visual data of the left eye at a sampling rate of 30 Hz (corresponding to a 33.3 ms time interval between successive visual data samplings of the left eye such as L1 and L3 or L3 and L5 or L5 and L7). Similarly, one or more tracking cameras of the right eye are illustrated as capturing the visual data of the right eye at a sampling rate of 30 Hz (as shown by 33.3 ms duration between successive samples such as R2 and R4 or R4 and R6). Because capture of the visual data of the left and right eyes is staggered, the combined sampling rate for capturing visual data of both eyes is 60 Hz (as shown, for example, by 16.7 ms time duration between successive captured and estimated samples, L1 and L2, respectively, for the left eye). Advantageously, the approach illustrated in FIG. 8 can double the sampling rate as compared to the approach of FIG. 7A. Also, the approach illustrated in FIG. 8 can reduce the sampling latency for each eye in half (due to the estimated samples) as compared to the approach of FIG. 7A. Additionally, the approach illustrated in FIG. 8 may not necessitate increases in the frame rate of one or more eye tracking cameras or increases in the power consumption, increases in the computing speed, increases in the use of computing resources (other than a small increase in computing resources for estimating visual data, as described below), or the like.

It has been observed that the left and right eyes can be strongly coupled. For example, blinks of the left and right eyes may occur in unison. As another example, saccades of the left and right eyes may occur in unison so that the eyes may move equally and in the same direction. Accordingly, in various situations, the vertical component of the gaze vector of the left and right eyes may be the same. As a result, estimation (or prediction) of the visual data of the eyes can be performed based on the principle that the difference between the left and right eyes (or vice versa) may be slow varying. In some cases, estimation can involve determining the difference between the visual data of the left and right eyes. The determined difference can be filtered (for example, using a low pass filter, such as by averaging) and subsequently used to estimate the visual data of an eye at a time instance during which the visual data of that eye was not captured (such as, during the time instances indicated by the light bars in FIG. 8). With this approach, differences between the vertical and horizontal movements of the left and right eyes can be accounted for.

In various implementations, estimation can involve determining a difference between the visual data of the left eye and a difference between the visual data of the right eye. The difference values can be determined from past visual data samples of the respective eyes. The difference values can be indicative of the differences between the horizontal components of the gaze vector of the left eye and the right eye. In some implementations, the determined difference values can be filtered (for example, averaged). Subsequently, the difference or filtered difference values can be used to determine a difference between visual data of the left and right eyes (for example, as provided in equations (1a) and (2a)). Visual data for the right eye can be estimated using visual data of the left eye and the difference between visual data of the left and right eyes (for example, as provided in equation 1(b)). Similarly, visual data for the left eye can be estimated using visual data of the right eye and the difference between visual data of the left and right eyes (for example, as provided in equation 2(b)). Estimation of the visual data for the right and left eyes can also involve using a prediction filter in some implementations.

As an example, visual data can be captured at time instances n=[0, 1, 2, 3, ..., N]. Visual data of the left eye can be captured at even-numbered time instances and be represented by a set L[n]. Visual data of the right eye can be captured at odd-numbered time instances and be represented by a set R[n]. In some cases, visual data of the right eye can be captured at even-numbered time instances and visual data of the left eye can be captured at odd-numbered time instances. The difference between the visual data of the two eyes can be represented by a set D[n]. For example, in some implementations, for even time instances (during which visual data of the left eye is captured while visual data of the right eye is not captured), visual data for the right eye R'[n] can be estimated as follows:

$$D[n]=(L[n]+L[n-2])/2-R[n-1] \quad (1a)$$

$$R'[n]=L[n]-D[n] \quad (1b)$$

For odd time instances (during which visual data of the right eye is captured while visual data of the left eye is not captured), visual data for the left eye L'[n] can be estimated as follows:

$$D[n]=L[n-1]-(R[n]+R[n-2])/2 \quad (2a)$$

$$L'[n]=R[n]+D[n] \quad (2b)$$

Accordingly, as described above, visual data for a first eye (e.g., the left eye) during a particular time can be estimated from visual data of the second eye (e.g., the right eye) captured during the particular time (e.g., $t_n$). In this example, the particular time ($t_n$) may be the third time in a sequence of three time instances ($t_n$, $t_{n-1}$, $t_{n-2}$). This third time, $t_n$, may be immediately preceded by a second time, $t_{n-1}$, which is immediately preceded by a first time, $t_{n-2}$. In some implementations such as discussed above, visual data for a first eye (e.g., the left eye) during third time, $t_n$, can be estimated from visual data for the first eye (e.g., the left eye) captured during the preceding time (e.g., $t_{n-1}$) and the average of video data for the second eye (e.g., right eye) captured during the current time (e.g., third time, $t_n$) and the preceding time at which video data is captured for the second eye, e.g., the first time, $t_{n-2}$. In some implementations, for example, the visual data for a first eye (e.g., the left eye) during third time, $t_n$, can be estimated from a difference between the visual data for the first eye (e.g., the left eye) captured during the preceding time (e.g., $t_{n-1}$) and this average of video data for the second eye. In some implementations, for example, the difference can be determined as a difference between 1) the averaged visual data of the second eye captured during the third time, $t_n$, and the first time, $t_{n-2}$, which corresponds to the preceding time during which the video data was captured for the second eye and 2) visual data for the first eye captured during a preceding time, $t_{n-1}$, (e.g., the time immediately preceding the third time, $t_n$, for capturing visual data of the eye). This difference can be combined with the visual data of the second eye (e.g., right eye) captured during the particular time, $t_n$, to estimate visual data for the first eye (e.g., left eye) during the particular time. In some implementations, the averaging can contribute to low pass filtering. Averaging can be representative of applying a low pass filter (for instance, to remove or limit error(s) due to noise). Of course, this approach can be applied to estimate visual data for the right eye during a time when video data is captured for the left eye. Likewise, the left eye may be the first eye and the right eye may be the second eye or the right eye may be the first eye and the left eye may be the second eye. As illustrated in FIG. 8, in various implementations, the left and right eye will alternate as the eyes for which video data is collected and video data is estimated as the eye tracking system progresses through a series of time instances.

In some implementations, additional samples of the visual data can be used for the estimation. For example, samples of the visual data going further back in time than the immediately preceding one or two time instances for capturing visual data of the eye can be used. Including more samples in the estimation can potentially improve the accuracy of the estimation. Accordingly, averaging over more than two time instances may be used in some implementation. Other methods for estimating may also be employed. In some cases, for example, Kalman filter, machine learning, deep learning, etc. can be used for the estimation.

In some implementations, the estimation problem can be stated generally as how to estimate visual data L'[n] and R'[n] from visual data previous samples, e.g., any one or more of L[n], R[n−1], L[n−2], R[n−3], L[n−4], etc. alternately captured by the respective eye tracking camera(s). The captured visual data samples can be somewhat noisy. The estimation problem can be solved using a Kalman filter, particularly if the nature of the noise and/or frequency content of the gaze vectors is known. The Kalman filter can be used to estimate a joint probability distribution of the gaze vectors of the left and right eyes and, based on the joint probability, estimate the visual data of the left and/or right eye at one or more time instances when the respective eye tracking camera(s) do not capture the visual data of the eye. The Kalman filter can perform estimation and noise removal.

In some cases, machine learning and/or deep learning can be used to estimate the visual data. A network (such as, a neural network) to estimate the visual data L'[n] and R'[n] can be created. The network can be trained using one or more datasets of visual data captured for simultaneously for both eyes. Such one or more datasets can include large amount of data. Subsequently, the trained network can be used estimate the visual data from the previous visual data samples, e.g., any one or more of L[n], R[n−1], L[n−2], R[n−3], L[n−4], etc. alternately captured by the respective eye tracking camera(s).

Experimental results indicate that alternate sampling at, for instance, a 30 Hz sampling rate for both the left and right eyes (with the estimation that uses the equations (1a)-(1b) and (2a)-(2b)) can result in at least 32% decrease in errors for detecting events, at least 50% drop in sampling latency for saccade detection, at least 50% drop in sampling latency for blink detection, or the like as compared to the sampling of each of the eyes at 30 Hz as illustrated in FIG. 7A. These improvements can be comparable with sampling each of the eyes at 60 Hz without alternate sampling as illustrated in FIG. 7B. Similar improvements have been obtained when using alternate sampling at 60 Hz sampling rate for each of the eyes (with the combined sampling rate of 120 Hz for both eyes) and using alternate sampling at 120 Hz sampling rate for each of the eyes (with the combined sampling rate of 240 Hz for both eyes).

Figure 9:
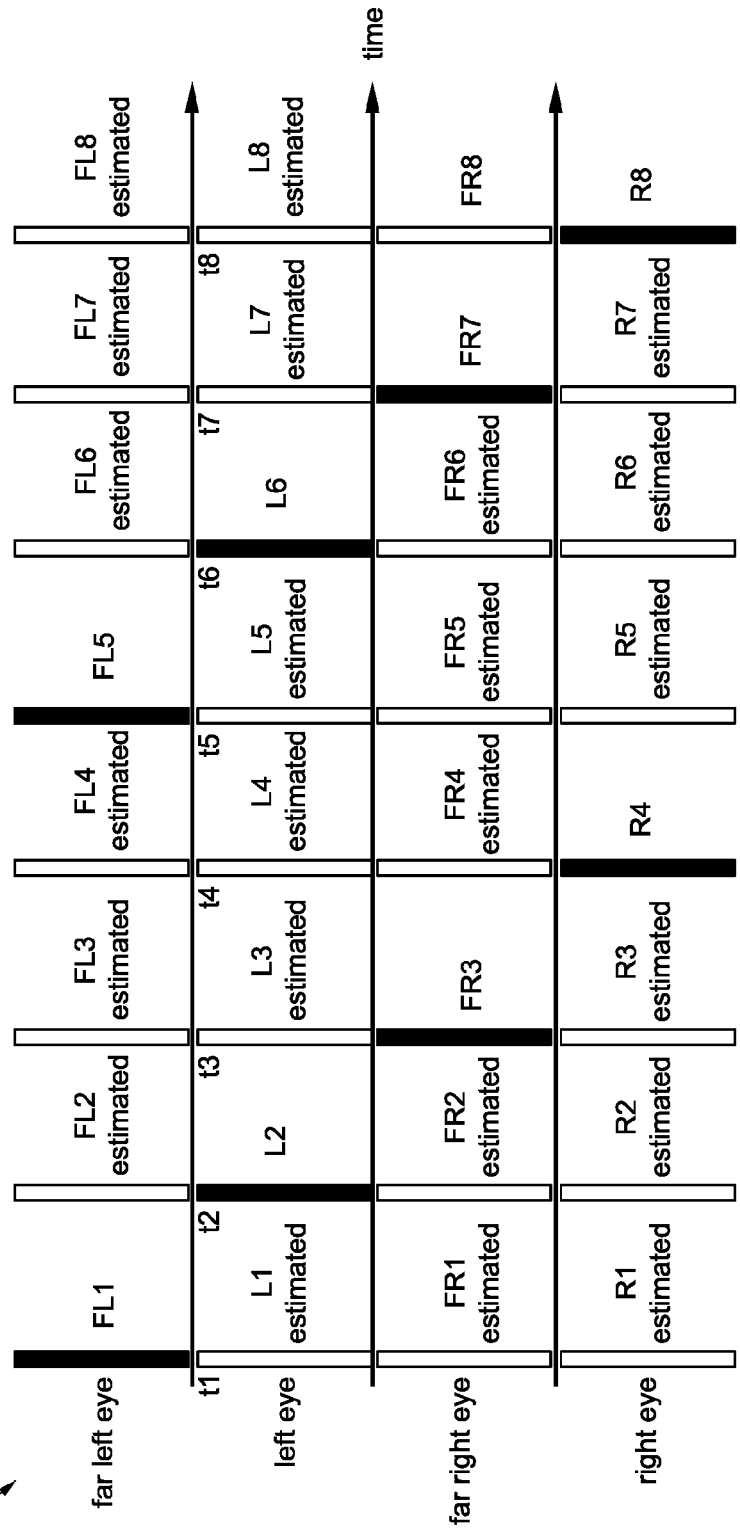
FIG. 9 is a graph that illustrates capturing visual data of a left eye and a right eye with multiple cameras for each of the eyes using alternate sampling.

FIG. 9 is a graph 900 illustrating capturing visual data of both eyes with multiple eye tracking cameras using alternate sampling. The graph 900 is similar to the graph 800 of FIG. 8 except that two eye tracking cameras per each eye capture visual data. For instance, a first eye tracking camera can be positioned on one side of an eye (such as, on the temporal side) and a second eye tracking camera can be positioned on the other side of the eye (such as, on the nasal side of the eye). Other positions are possible. For example, a first camera can be above the eye, closer to the forehead, and a second camera can be below the eye, closer to the cheek. Accordingly, two eye tracking cameras for each of the eyes can be used for a total of four eye tracking cameras for two eyes.

In FIG. 9, both the eye tracking cameras for the left eye as well as both the tracking cameras for the right eye are configured to alternately capture visual data for each of the eyes. And the eye tracking cameras for the left eye are also configured to alternate with the eye tracking cameras of the right eye. According, in this example, the four cameras (two for left eye and two for right eye) are configured to alternately capture visual data for each of the eyes. For example, as shown, visual data for the left eye (FL1) is captured by a first left eye tracking camera, which may be positioned farther from the left eye (such as, on the left temporal side, left nasal side, or at another position as described herein), at an initial time (such as, t1). During such time, visual data for the left eye is not captured by a second left eye tracking camera, which may be positioned closer to the left eye (such as, on the left nasal side, left temporal side, or at another position as described herein) and visual data for the right eye is not captured. At the next time (such as, t2), visual data for the left eye (L2) is captured by the second left eye tracking camera. During such time, visual data for the left eye is not captured by the first left eye tracking camera and visual data for the right eye is not captured. At the next time (such as, at t3), visual data for the right eye (FR3) is captured by a first right eye tracking camera, which may be positioned farther from the right eye (such as, on the right temporal side, right nasal side, or at another position as described herein). During such time, visual data for the left eye is not captured and visual data for the right eye is not captured by a second right eye tracking camera, which may be positioned closer to the right eye (such as, on the right nasal side, right temporal side, or at another position as described herein). At the next time (such as, at t4), visual data for the right eye (FR4) is captured by the second right eye tracking camera. During such time, visual data for the left eye is not captured and visual data for the right eye is not captured by the first eye tracking camera. As illustrated in FIG. 9, this process can continue for the subsequent time instances t5, t6, t7, t8, and so on. The arrangement and order that cameras capture video data can be different and can vary with time. Other variations are possible.

As a result, one or more eye tracking cameras for each of the eyes alternate capture of visual data. In the example illustrated in FIG. 9, four sampling intervals are employed to capture a complete visual data set for both of the eyes using the four eye tracking cameras. Provided that, for instance, each eye tracking camera operates at the frame rate of 30 fps (or sampling rate of 30 Hz), the combined frame rate for capturing visual data of both of the eyes by the four eye tracking cameras in the illustrated example is 240 fps (or 240 Hz).

Similar to FIG. 8, in the graph 900 dark bars represent visual data being captured by one or more eye tracking cameras for the left and right eyes. Light bars in the graph 900 represent the estimation of visual data for the left and right eyes. Estimation of the visual data can be performed similarly to any of the approaches described herein as well as possibly using other approaches. Multiple eye tracking cameras for each eye can capture more visual data samples than one eye tracking camera per eye. For example, visual data samples FL[n], L[n−1], FR[n−3], R[n−4], FL[n−5], etc. can be captured by the multiple eye tracking cameras, as illustrated in FIG. 9. The captured visual data samples may have different noise properties, such that the accuracy of each sample could be different as well as varying over time. For example, if a user is looking far to the left, the eye tracking camera positioned at the left nasal side may not have a clear view of the left eye, which may result in a noisy visual data sample captured by such camera. However, the eye tracking camera positioned at the left temporal side may have a clear view of the left eye and, as a result, capture a less noisy visual data sample of the left eye. The visual data sample captured by the eye tracking camera positioned at the left temporal side can be used, for instance, to estimate visual data of the right eye (such as, R'[n] or FR'[n]).

Example Method for Eye Tracking

Figure 10:
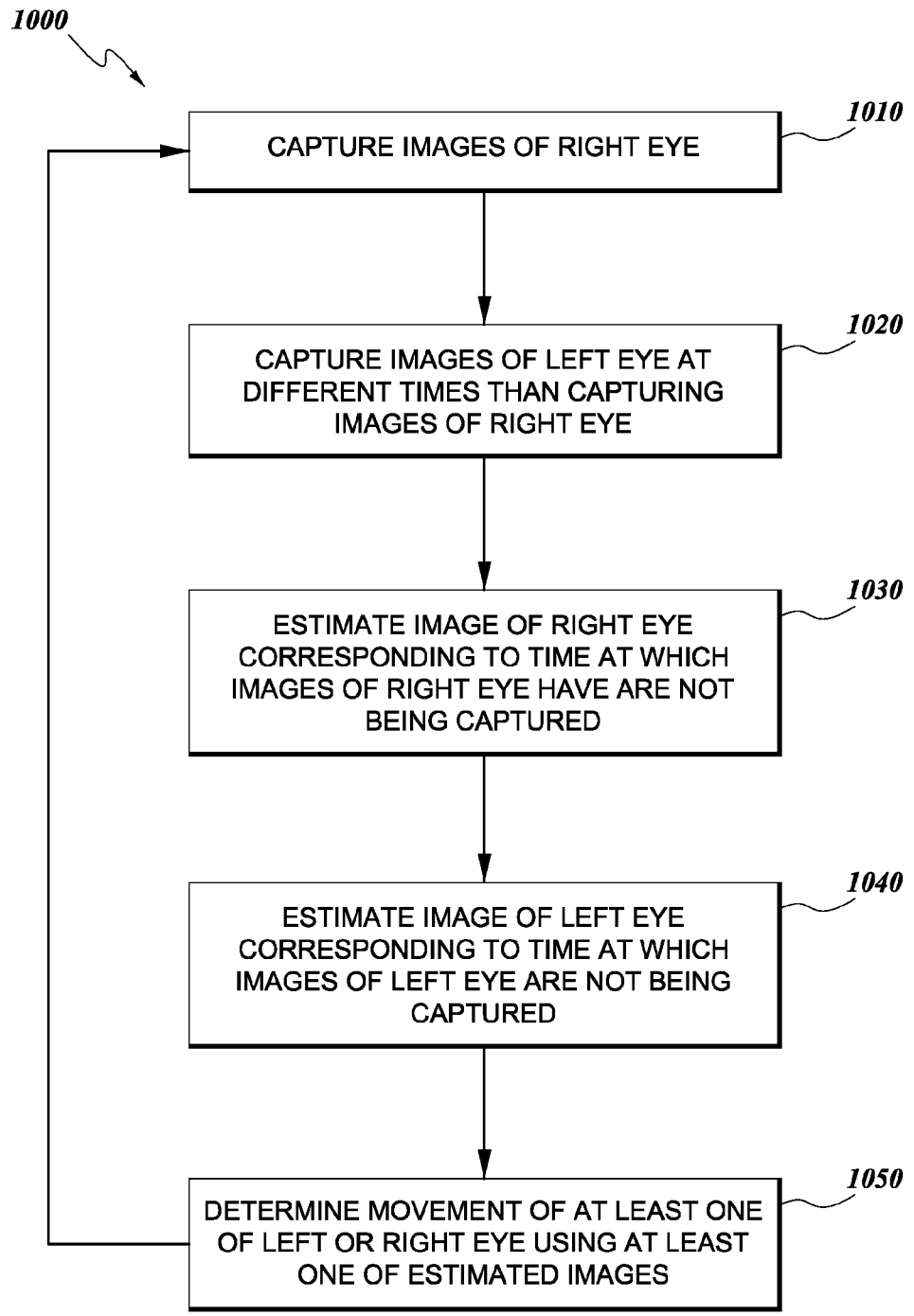
FIG. 10 is a flow chart that illustrates of an example method for eye tracking.

FIG. 10 is a flowchart that illustrates an example method 1000 for eye tracking. The method 1000 can be performed by implementations of the wearable display system 200, 400, or 600, for example, using the eye tracking system 601 described with reference to FIG. 6 or other configurations. In various implementations of the method 1000, the blocks described below can be performed in any suitable order or sequence, blocks can be omitted, combined, or rearranged, other blocks can be added or any combination of these.

At block 1010, the method 1000 can capture visual data of the left eye (or, in some cases, of the right eye) using one or more eye tracking cameras. At block 1020, the method 1000 can capture visual data of the right eye (or, in some cases, of the left eye) using one or more eye tracking cameras. As described herein, one or more eye tracking cameras can alternate capture of visual data of the right and left eye. As a result, at block 1010, visual data of the right eye may not be captured. Similarly, at block 1020, visual data of the left eye may not be captured. With reference to FIG. 8, for example, block 1010 can correspond to the time t1 and block 1020 can correspond to the time t2.

At block 1030, the method 1000 can estimate visual data of the left eye at one or more time instances during which the visual data of the left eye is not captured by one or more eye tracking cameras. At block 1040, the method 1000 can estimate visual data of the right eye at one or more time instances during which the visual data of the right eye is not captured by one or more eye tracking cameras. Any of the estimation techniques described herein can be utilized by the method 1000.

At block 1050, the method 1000 can determine eye movement (or pose) of the left and/or right eye based on the estimated visual data and/or captured visual data. One or more iterations of data capture for collecting video data and/or estimation may be repeated and used to determine eye movement. One or more processors of the wearable display system can analyze the estimated visual data and/or captured visual data to determine positions and movement of the glints for eye tracking, as described herein. As explained herein, eye tracking can assist in determining how to render virtual content for presentation to the user. In some cases, eye tracking may determine eye pose for the eyes separately, thereby allowing presentation of virtual content to the respective eye to be dynamically tailored to that eye.

ADDITIONAL EXAMPLES

Example 1. A wearable display system comprising:
a head-mounted display configured to present virtual content by outputting light to an eye of a wearer of the head-mounted display;
at least one light source configured to direct light toward the eye of the wearer;
a right eye tracking camera configured to capture a first plurality of visual data of a right eye of the wearer at a first sampling rate;
a left eye tracking camera configured to capture a second plurality of visual data of a left eye of the wearer at a second sampling rate, the second plurality of visual data captured during different sampling times than the first plurality of visual data; and
processing electronics communicatively coupled to the head-mounted display and to the right and left eye tracking cameras, the processing electronics configured to:
based on at least some visual data of the first and second plurality of visual data, estimate visual data of the right eye at a sampling time during which visual data of the first plurality of visual data is not being captured;
based on at least some visual data of the first and second plurality of visual data, estimate visual data of the left eye at a sampling time during which visual data of the second plurality of visual data is not being captured;
determine eye movement of at least one of the right or left eye, the determination of the eye movement of the right eye based on at least some of the estimated visual data of the right eye and at least some visual data of the first plurality of visual data of the right eye, and the determination of the eye movement of the left eye based on at least some of the estimated visual data of the left eye and at least some visual data of the second plurality of visual data of the left eye; and
cause the head-mounted display to present the virtual content based on the eye movement of at least one of the right or left eye.

Example 2. The wearable display system of example 1, wherein the at least one light source comprises an infrared light source.

Example 3. The wearable display system of example 1 or example 2, wherein the at least one light source comprises a first light source configured to direct light toward the left eye and a second light source configured to direct light toward the right eye.

Example 4. The wearable display system of any one of examples 1 to 3, wherein a combined sampling rate of the right and left eye tracking cameras comprises an aggregate of the first and second sampling rates.

Example 5. The wearable display system of any one of examples 1 to 4, wherein the first sampling rate is equal to the second sampling rate.

Example 6. The wearable display system of any one of examples 1 to 5, wherein the right and left eye tracking cameras are configured to alternate capture of the first and second pluralities of visual data.

Example 7. The wearable display system of any one of examples 1 to 6, wherein the first and second sampling rates comprise 30 Hz.

Example 8. The wearable display system of example 7, wherein a combined sampling rate of the right and left eye tracking cameras comprises 60 Hz.

Example 9. The wearable display system of any one of examples 1 to 8, wherein processing electronics is configured to estimate the visual data of the right eye or the left eye based on a determination of a difference between visual data of the first plurality of visual data of the right eye and visual data of the second plurality of visual data of the left eye.

Example 10. The wearable display system of example 9, wherein the processing electronics is further configured to:
estimate the visual data of the right eye based on a first difference between visual data of the second plurality of visual data of the left eye captured during the sampling time of the estimated visual data and visual data of the first plurality of visual data of the right eye captured during a sampling time immediately prior to the sampling time of the estimated visual data; and
estimate the visual data of the left eye based on a second difference between visual data of the first plurality of visual data of the right eye captured during the sampling time of the estimated visual data and visual data of the second plurality of visual data of the left eye captured during a sampling time immediately prior to the sampling time of the estimated visual data.

Example 11. The wearable display system of any one of examples 9 to 10, wherein the processing electronics is further configured to:
estimate the visual data of the right eye based on the difference and visual data of the first plurality of visual data of the right eye captured during a sampling time immediately prior to the sampling time of the estimated visual data; and
estimate the visual data of the left eye based on the difference and visual data of the second plurality of visual data of the left eye captured during a sampling time immediately prior to the sampling time of the estimated visual data.

Example 12. The wearable display system of any of one of examples 9 to 11, wherein the processing electronics is further configured to estimate the visual data of the right or left eye based on filtering the difference.

Example 13. The wearable display system of example 12, wherein filtering the difference comprises averaging.

Example 14. A method for eye tracking comprising:
capturing with a first camera a first plurality of visual data of a right eye at a first sampling rate;
capturing with a second camera a second plurality of visual data of a left eye at a second sampling rate, the second plurality of visual data captured during different sampling times than the first plurality of visual data; and by processing electronics:
based on at least some visual data of the first and second plurality of visual data, estimating visual data of at least one of the right or left eye at a sampling time during which visual data of an eye for which the visual data is being estimated are not being captured; and
determining eye movement of the eye based on at least some of the estimated visual data and at least some visual data of the first or second plurality of visual data.

Example 15. The method of example 14, further comprising, by the processing electronics, causing a display to render virtual content based at least partly on the eye movement.

Example 16. The method of any of one of examples 14 to 15, wherein determining the eye movement comprises:
determining eye movement of the right eye based on at least some of the estimated visual data of the right eye and at least some visual data of the first plurality of visual data of the right eye; and
determining eye movement of the left eye based on at least some of the estimated visual data of the left eye and at least some visual data of the second plurality of visual data of the left eye.

Example 17. The method of any one of examples 14 to 16, wherein a combined sampling rate of the first and second cameras comprises an aggregate of the first and second sampling rates.

Example 18. The method of any one of examples 14 to 17, wherein the first sampling rate is equal to the second sampling rate.

Example 19. The method of any one of examples 14 to 18, wherein the first camera and the second camera alternately capture the first and second pluralities of visual data.

Example 20. The method of any one of examples 14 to 18, wherein the first and second sampling rates comprise 30 Hz.

Example 21. The method of example 19, wherein a combined sampling rate of the first and second cameras comprises 60 Hz.

Example 22. The method of any one of examples 14 to 21, wherein estimating the visual data of comprises determining a difference between visual data of the first plurality of visual data of the right eye and visual data of the second plurality of visual data of the left eye.

Example 23. The method of example 22, wherein: estimating the visual data of the right eye comprises:
estimating the visual data of the right eye comprises determining a first difference between visual data of the second plurality of visual data of the left eye captured during the sampling time of the estimated visual data and visual data of the first plurality of visual data of the right eye captured during a sampling time prior to the sampling time of the estimated visual data; and
estimating the visual data of the left eye comprises determining a second difference between visual data of the first plurality of visual data of the right eye captured during the sampling time of the estimated visual data and visual data of the second plurality of visual data of the left eye captured during a sampling time prior to the sampling time of the estimated visual data.

Example 24. The method of example 23, wherein:
the sampling time of the visual data of the first plurality of visual data of the right eye is immediately prior to the sampling time of the estimated visual data; and
the sampling time of the visual data of the second plurality of visual data of the left eye is immediately prior to the sampling time of the estimated visual data.

Example 25. The method of any one of examples 22 to 24, further comprising, by the processing electronics:
estimating the visual data of the right eye based on the difference and visual data of the first plurality of visual data of the right eye captured during a sampling time prior to the sampling time of the estimated visual data; and
estimating the visual data of the left eye based on the difference and visual data of the second plurality of visual data of the left eye captured during a sampling time prior to the sampling time of the estimated visual data.

Example 26. The method of example 25, wherein:
the sampling time of the visual data of the first plurality of visual data of the right eye is immediately prior to the sampling time of the estimated visual data; and
the sampling time of the visual data of the second plurality of visual data of the left eye is immediately prior to the sampling time of the estimated visual data.

Example 27. The method of any one of examples 22 to 26, further comprising filtering the difference by a low pass filter.

Example 28. An eye tracking system comprising:
a first camera configured to capture a first plurality of visual data of a right eye of a user at a first sampling rate;
a second camera configured to capture a second plurality of visual data of a left eye of the user at a second sampling rate, the second plurality of visual data captured during different sampling times than the first plurality of visual data; and
processing electronics communicatively coupled to the first and second cameras, the processing electronics configured to:
based on at least some visual data of the first and second plurality of visual data, estimate visual data of at least one of the right or left eye at a sampling time during which visual data of an eye for which the visual data is being estimated are not being captured; and
determine eye movement of the eye based on at least some of the estimated visual data and at least some visual data of the first or second plurality of visual data.

Example 29. The eye tracking system of example 28, wherein processing electronics is configured to:
determine eye movement of the right eye based on at least some of the estimated visual data of the right eye and at least some visual data of the first plurality of visual data of the right eye; and
determine eye movement of the left eye based on at least some of the estimated visual data of the left eye and at least some visual data of the second plurality of visual data of the left eye.

Example 30. The eye tracking system of any one of examples 28 to 29, wherein a combined sampling rate of the first and second cameras comprises an aggregate of the first and second sampling rates.

Example 31. The eye tracking system of any one of examples 28 to 30, wherein the first sampling rate is equal to the second sampling rate.

Example 32. The eye tracking system of any one of examples 28 to 31, wherein the first and second cameras are configured to alternate capture of the first and second pluralities of visual data.

Example 33. The eye tracking system of any one of examples 28 to 32, wherein the first and second sampling rates comprise 30 Hz.

Example 34. The eye tracking system of example 33, wherein a combined sampling rate of the first and second cameras comprises 60 Hz.

Example 35. The eye tracking system of any one of examples 28 to 34, wherein the processing electronics is configured to estimate the visual data based on a determination of difference between at least one visual data of the first plurality of visual data of the right eye and at least one visual data of the second plurality of visual data of the left eye.

Example 36. The eye tracking system of example 35, wherein the processing electronics is further configured to:
  estimate the visual data of the right eye based on a determination of a first difference between visual data of the second plurality of visual data of the left eye captured during the sampling time of the estimated visual data and visual data of the first plurality of visual data of the right eye captured during a sampling time prior to the sampling time of the estimated visual data; and
  estimate the visual data of the left eye based on a determination of a second difference between visual data of the first plurality of visual data of the right eye captured during the sampling time of the estimated visual data and visual data of the second plurality of visual data of the left eye captured during a sampling time prior to the sampling time of the estimated visual data.

Example 37. The eye tracking system of example 36, wherein:
  the sampling time of the visual data of the first plurality of visual data of the right eye is immediately prior to the sampling time of the estimated visual data; and
  the sampling time of the visual data of the second plurality of visual data of the left eye is immediately prior to the sampling time of the estimated visual data.

Example 38. The eye tracking system of any one of examples 35 to 37, wherein the processing electronics is further configured to:
  estimate the visual data of the right eye based on the difference and visual data of the first plurality of visual data of the right eye captured during a sampling time prior to the sampling time of the estimated visual data; and
  estimate the visual data of the left eye based on the difference and visual data of the second plurality of visual data of the left eye captured during a sampling time prior to the sampling time of the estimated visual data.

Example 39. The eye tracking system of example 38, wherein:
  the sampling time of the visual data of the first plurality of visual data of the right eye is immediately prior to the sampling time of the estimated visual data; and
  the sampling time of the visual data of the second plurality of visual data of the left eye is immediately prior to the sampling time of the estimated visual data.

Example 40. The eye tracking system of any one of examples 35 to 39, wherein the processing electronics is further configured to estimate the visual data of the right or left eye based on filtering the difference using a low pass filter.

Example 41. A wearable display system comprising the eye tracking system of any one of examples 28 to 40 and a display configured to present virtual content, wherein the processing electronics is communicatively coupled to the display and further configured to cause the display to present the virtual content based on the eye movement.

Example 42. The wearable display system of example 41, comprising a head mounted display.

Example 43. A wearable display system comprising:
  a frame configured to be supported on a head of a wearer;
  a head-mounted display disposed on the frame, said display configured to present virtual image content to the wearer by outputting light to an eye of the wearer;
  a right eye tracking camera configured to capture a first plurality of visual data of a right eye of the wearer; and
  a left eye tracking camera configured to capture a second plurality of visual data of a left eye of the wearer,
  wherein the second plurality of visual data is captured during different sampling times than the first plurality of visual data, said left eye tracking camera not capturing visual data during periods when said right eye tracking camera is capturing visual data and said right eye tracking camera not capturing visual data during periods when said left eye tracking camera is capturing visual data.

Example 44. The wearable display system of example 43, further comprising at least one light source configured to direct light toward the eye of the wearer.

Example 45. The wearable display system of example 44, wherein the at least one light source comprises an infrared light source.

Example 46. The wearable display system of any one of examples 44 to 45, wherein the at least one light source comprises a first light source configured to direct light toward the left eye and a second light source configured to direct light toward the right eye.

Example 47. The wearable display system of any one of examples 43 to 46, wherein a combined sampling rate of the right and left eye tracking cameras comprises an aggregate of sampling rates of the left and right eye tracking cameras.

Example 48. The wearable display system of example 47, wherein the sampling rate of the left eye tracking camera is equal to the sampling rate of the right eye tracking camera.

Example 49. The wearable display system of example 48, wherein the sampling rate of the left and right eye tracking cameras comprises 30 Hz.

Example 50. The wearable display system of example 49, wherein a combined sampling rate of the left and right eye tracking cameras comprises 60 Hz.

Example 51. The wearable display system of any one of examples 43 to 50, wherein the right and left eye tracking cameras are configured to alternate capture of the first and second pluralities of visual data.

Example 52. The wearable display system of any one of examples 43 or 51, further comprising processing electronics communicatively coupled to the head-mounted display and to the right and left eye tracking cameras.

Example 53. The wearable display system of example 52, wherein the processing electronics is configured to estimate visual data of the right eye at a sampling time during which visual data of the first plurality of visual data is not being captured and estimate visual data of the left eye at a sampling time during which visual data of the second plurality of visual data is not being captured.

Example 54. The wearable display system of any one of examples 52 or 53, wherein the processing electronics is configured to:
- based on at least some visual data, estimate visual data of the right eye at a sampling time during which visual data of the first plurality of visual data is not being captured; and
- based on at least some visual data, estimate visual data of the left eye at a sampling time during which visual data of the second plurality of visual data is not being captured.

Example 55. The wearable display system of any one of examples 52 to 54, wherein the processing electronics is configured to:
- based on at least some visual data of the first and second plurality of visual data, estimate visual data of the right eye at a sampling time during which visual data of the first plurality of visual data is not being captured; and
- based on at least some visual data of the first and second plurality of visual data, estimate visual data of the left eye at a sampling time during which visual data of the second plurality of visual data is not being captured.

Example 56. The wearable display system of any one of examples 52 to 55, wherein the processing electronics is configured to determine eye movement of at least one of the right or left eye using captured visual data.

Example 57. The wearable display system of any of examples 52 to 56, wherein the processing electronics is configured to determine eye movement of at least one of the right or left eye, the determination of the eye movement of the right eye based on at least some estimated visual data of the right eye and at least some visual data of the first plurality of visual data of the right eye, and the determination of the eye movement of the left eye based on at least some estimated visual data of the left eye and at least some visual data of the second plurality of visual data of the left eye.

Example 58. The wearable display system of any one of examples 52 to 57, wherein the processing electronics is configured to estimate visual data of the right eye at a sampling time during which visual data of the first plurality of visual data is not being captured and estimate visual data of the left eye at a sampling time during which visual data of the second plurality of visual data is not being captured based on a determination of a difference between visual data of the first plurality of visual data and visual data of the second plurality of visual data.

Example 59. The wearable display system of example 58, wherein the processing electronics is further configured to:
- estimate the visual data of the right eye based on a first difference between visual data of the second plurality of visual captured during the sampling time of the estimated visual data and visual data of the first plurality of visual data captured during a sampling time immediately prior to the sampling time of the estimated visual data; and
- estimate the visual data of the left eye based on a second difference between visual data of the first plurality of visual data captured during the sampling time of the estimated visual data and visual data of the second plurality of visual data captured during a sampling time immediately prior to the sampling time of the estimated visual data.

Example 60. The wearable display system of any one of examples 58 to 59, wherein the processing electronics is further configured to:
- estimate the visual data of the right eye based on the difference and visual data of the first plurality of visual data captured during a sampling time immediately prior to the sampling time of the estimated visual data; and
- estimate the visual data of the left eye based on the difference and visual data of the second plurality of visual data of captured during a sampling time immediately prior to the sampling time of the estimated visual data.

Example 61. The wearable display system of any of examples 58 to 60, wherein the processing electronics is further configured to estimate the visual data of the right or left eye based on filtering the difference.

Example 62. The wearable display system of example 61, wherein filtering the difference comprises averaging.

Example 63. A wearable display system comprising:
- a head-mounted display configured to present virtual content by outputting light to an eye of a wearer of the head-mounted display;
- a right eye tracking camera configured to capture a first plurality of visual data of a right eye of the wearer;
- a left eye tracking camera configured to capture a second plurality of visual data of a left eye of the wearer; and
- processing electronics communicatively coupled to the head-mounted display and to the right and left eye tracking cameras, the processing electronics configured to:
  - based on at least some visual data, estimate visual data of the right eye;
  - based on at least some visual data, estimate visual data of the left eye.

Example 64. The wearable display system of example 63, further comprising at least one light source configured to direct light toward the eye of the wearer.

Example 65. The wearable display system of example 64, wherein the at least one light source comprises an infrared light source.

Example 66. The wearable display system of any one of examples 64 to 65, wherein the at least one light source comprises a first light source configured to direct light toward the left eye and a second light source configured to direct light toward the right eye.

Example 67. The wearable display system of any one of examples 63 to 66, wherein a combined sampling rate of the right and left eye tracking cameras comprises an aggregate of sampling rates of the left and right eye tracking cameras.

Example 68. The wearable display system of example 67, wherein the sampling rate of the left eye tracking camera is equal to the sampling rate of the right eye tracking camera.

Example 69. The wearable display system of example 68, wherein the sampling rate of the left and right eye tracking cameras comprises 30 Hz.

Example 70. The wearable display system of example 69, wherein a combined sampling rate of the left and right eye tracking cameras comprises 60 Hz.

Example 71. The wearable display system of any one of examples 63 to 70, wherein the right and left eye tracking cameras are configured to alternate capture of the first and second pluralities of visual data.

Example 72. The wearable display system of any one of examples 63 or 71, wherein the processing electronics is configured to estimate visual data of the right eye at a sampling time during which visual data of the first plurality of visual data is not being captured and estimate visual data of the left eye at a sampling time during which visual data of the second plurality of visual data is not being captured.

Example 73. The wearable display system of any one of examples 63 to 72, wherein the processing electronics is configured to:
  based on at least some visual data of the second plurality of visual data, estimate visual data of the right eye; and
  based on at least some visual data of the first plurality of visual data, estimate visual data of the left eye.

Example 74. The wearable display system of any one of examples 63 to 73, wherein the processing electronics is configured to:
  based on at least some visual data of the first plurality of visual data, estimate visual data of the right eye; and
  based on at least some visual data of the second plurality of visual data, estimate visual data of the left eye.

Example 75. The wearable display system of any one of examples 63 or 71, wherein processing electronics is configured to:
  based on at least some visual data of the first and second plurality of visual data, estimate visual data of the right eye for a sampling time during which visual data of the first plurality of visual data is not being captured;
  based on at least some visual data of the first and second plurality of visual data, estimate visual data of the left eye for a sampling time during which visual data of the second plurality of visual data is not being captured.

Example 76. The wearable display system of any one of examples 63 to 75, wherein the processing electronics is configured to determine eye movement of at least one of the right or left eye based on captured visual data.

Example 77. The wearable display system of any one of examples 63 to 76, wherein the processing electronics is configured to determine eye movement of at least one of the right or left eye, the determination of the eye movement of the right eye based on at least some estimated visual data of the right eye and at least some visual data of the first plurality of visual data of the right eye, and the determination of the eye movement of the left eye based on at least some estimated visual data of the left eye and at least some visual data of the second plurality of visual data of the left eye.

Example 78. The wearable display system of any one of examples 63 to 77, wherein the processing electronics is configured to estimate visual data of the right eye at a sampling time during which visual data of the first plurality of visual data is not being captured and estimate visual data of the left eye at a sampling time during which visual data of the second plurality of visual data is not being captured based on a determination of a difference between visual data of the first plurality of visual data and visual data of the second plurality of visual data.

Example 79. The wearable display system of example 78, wherein the processing electronics is further configured to:
  estimate the visual data of the right eye based on a first difference between visual data of the second plurality of visual captured during the sampling time of the estimated visual data and visual data of the first plurality of visual data captured during a sampling time immediately prior to the sampling time of the estimated visual data; and
  estimate the visual data of the left eye based on a second difference between visual data of the first plurality of visual data captured during the sampling time of the estimated visual data and visual data of the second plurality of visual data captured during a sampling time immediately prior to the sampling time of the estimated visual data.

Example 80. The wearable display system of any one of examples 78 to 79, wherein the processing electronics is further configured to:
  estimate the visual data of the right eye based on the difference and visual data of the first plurality of visual data captured during a sampling time immediately prior to the sampling time of the estimated visual data; and
  estimate the visual data of the left eye based on the difference and visual data of the second plurality of visual data of captured during a sampling time immediately prior to the sampling time of the estimated visual data.

Example 81. The wearable display system of any one of examples 78 to 80, wherein the processing electronics is further configured to estimate the visual data of the right or left eye based on filtering the difference.

Example 82. The wearable display system of example 81, wherein filtering the difference comprises averaging.

Example 83. A method of using and/or operating a system of any of the preceding examples.

Example 84. An apparatus and/or method as illustrated and/or described.

Additional Considerations

Each of the processes, methods, and algorithms described herein and/or depicted in the attached figures may be embodied in, and fully or partially automated by, code modules executed by one or more physical computing systems, hardware computer processors, application-specific circuitry, and/or electronic hardware configured to execute specific and particular computer instructions. For example, computing systems can include general purpose computers (e.g., servers) programmed with specific computer instructions or special purpose computers, special purpose circuitry, and so forth. A code module may be compiled and linked into an executable program, installed in a dynamic link library, or may be written in an interpreted programming language. In some implementations, particular operations and methods may be performed by circuitry that is specific to a given function.

Further, certain implementations of the functionality of the present disclosure are sufficiently mathematically, computationally, or technically complex that application-specific hardware or one or more physical computing devices (utilizing appropriate specialized executable instructions) may be necessary to perform the functionality, for example, due to the volume or complexity of the calculations involved or to provide results substantially in real-time. For example, animations or video may include many frames, with each frame having millions of pixels, and specifically programmed computer hardware is necessary to process the video data to provide a desired image processing task or application in a commercially reasonable amount of time. Additionally, real-time eye-tracking for an AR, MR, VR wearable device is computationally challenging, and the eye tracking techniques disclosed herein may utilize efficient CPUs, GPUs, ASICs, or FPGAs.

Code modules or any type of data may be stored on any type of non-transitory computer-readable medium, such as physical computer storage including hard drives, solid state memory, random access memory (RAM), read only memory (ROM), optical disc, volatile or non-volatile storage, combinations of the same and/or the like. The methods and modules (or data) may also be transmitted as generated data signals (e.g., as part of a carrier wave or other analog or digital propagated signal) on a variety of computer-readable transmission mediums, including wireless-based and wired/cable-based mediums, and may take a variety of forms (e.g., as part of a single or multiplexed analog signal, or as multiple discrete digital packets or frames). The results of the disclosed processes or process steps may be stored, persistently or otherwise, in any type of non-transitory, tangible computer storage or may be communicated via a computer-readable transmission medium.

Any processes, blocks, states, steps, or functionalities in flow diagrams described herein and/or depicted in the attached figures should be understood as potentially representing code modules, segments, or portions of code which include one or more executable instructions for implementing specific functions (e.g., logical or arithmetical) or steps in the process. The various processes, blocks, states, steps, or functionalities can be combined, rearranged, added to, deleted from, modified, or otherwise changed from the illustrative examples provided herein. In some embodiments, additional or different computing systems or code modules may perform some or all of the functionalities described herein. The methods and processes described herein are also not limited to any particular sequence, and the blocks, steps, or states relating thereto can be performed in other sequences that are appropriate, for example, in serial, in parallel, or in some other manner. Tasks or events may be added to or removed from the disclosed example embodiments. Moreover, the separation of various system components in the implementations described herein is for illustrative purposes and should not be understood as requiring such separation in all implementations. It should be understood that the described program components, methods, and systems can generally be integrated together in a single computer product or packaged into multiple computer products. Many implementation variations are possible.

The processes, methods, and systems may be implemented in a network (or distributed) computing environment. Network environments include enterprise-wide computer networks, intranets, local area networks (LAN), wide area networks (WAN), personal area networks (PAN), cloud computing networks, crowd-sourced computing networks, the Internet, and the World Wide Web. The network may be a wired or a wireless network or any other type of communication network.

The systems and methods of the disclosure each have several innovative aspects, no single one of which is solely responsible or required for the desirable attributes disclosed herein. The various features and processes described above may be used independently of one another, or may be combined in various ways. All possible combinations and subcombinations are intended to fall within the scope of this disclosure. Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

Certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. No single feature or group of features is necessary or indispensable to each and every embodiment.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y and at least one of Z to each be present.

Similarly, while operations may be depicted in the drawings in a particular order, it is to be recognized that such operations need not be performed in the particular order shown or in sequential order, or that all illustrated operations be performed, to achieve desirable results. Further, the drawings may schematically depict one more example processes in the form of a flowchart. However, other operations that are not depicted can be incorporated in the example methods and processes that are schematically illustrated. For example, one or more additional operations can be performed before, after, simultaneously, or between any of the illustrated operations. Additionally, the operations may be rearranged or reordered in other implementations. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products. Additionally, other implementations are within the scope of the following claims. In some cases, the actions recited in the claims can be performed in a different order and still achieve desirable results.

What is claimed is:

1. A wearable display system, comprising:
a head-mounted display configured to present virtual content by outputting light to an eye of a wearer of the head-mounted display;
at least one light source configured to direct light toward the eye of the wearer; a right eye tracking camera configured to capture a first plurality of visual data of a right eye of the wearer at a first sampling rate;
a left eye tracking camera configured to capture a second plurality of visual data of a left eye of the wearer at a second sampling rate, the second plurality of visual data captured during different sampling times than the first plurality of visual data; and
processing electronics communicatively coupled to the head-mounted display and to the right eye tracking camera and left eye tracking camera, the processing electronics configured to:
based on at least some visual data of the first plurality of visual data and the second plurality of visual data, estimate visual data of the right eye at a sampling time during which visual data of the first plurality of visual data is not being captured;
based on at least some visual data of the first plurality of visual data and the second plurality of visual data, estimate visual data of the left eye at a sampling time during which visual data of the second plurality of visual data is not being captured;
determine eye movement of at least one of the right eye or the left eye, wherein a determination of the eye movement of the right eye is based on at least some of the estimated visual data of the right eye and at least some visual data of the first plurality of visual data of the right eye, and wherein a determination of the eye movement of the left eye is based on at least some of the estimated visual data of the left eye and at least some visual data of the second plurality of visual data of the left eye; and
cause the head-mounted display to present virtual content based on the eye movement of at least one of the right eye or the left eye.

2. The wearable display system of claim 1, wherein the at least one light source comprises an infrared light source.

3. The wearable display system of claim 1, wherein the at least one light source comprises a first light source configured to direct light toward the left eye and a second light source configured to direct light toward the right eye.

4. The wearable display system of claim 1, wherein a combined sampling rate of the right eye tracking camera and the left eye tracking camera comprises an aggregate of the first sampling rate and the second sampling rate.

5. The wearable display system of claim 1, wherein the first sampling rate is equal to the second sampling rate.

6. The wearable display system of claim 1, wherein the right eye tracking camera and the left eye tracking camera are configured to alternate capture of the first plurality of visual data and the second plurality of visual data.

7. The wearable display system of claim 1, wherein the first sampling rate and the second sampling rate comprise 30 Hz.

8. The wearable display system of claim 4, wherein a combined sampling rate of the right eye tracking camera and the left eye tracking camera comprises 60 Hz.

9. The wearable display system of claim 1, wherein the processing electronics are configured to estimate the visual data of the right eye or the left eye based on a determination of a difference between visual data of the first plurality of visual data of the right eye and visual data of the second plurality of visual data of the left eye.

10. The wearable display system of claim 9, wherein the processing electronics are further configured to:
estimate the visual data of the right eye based on a first difference between visual data of the second plurality of visual data of the left eye captured during the sampling time of the estimated visual data and visual data of the first plurality of visual data of the right eye captured during a sampling time immediately prior to the sampling time of the estimated visual data; and
estimate the visual data of the left eye based on a second difference between visual data of the first plurality of visual data of the right eye captured during the sampling time of the estimated visual data and visual data of the second plurality of visual data of the left eye captured during a sampling time immediately prior to the sampling time of the estimated visual data.

11. The wearable display system of claim 9, wherein the processing electronics are further configured to:
estimate the visual data of the right eye based on the difference and visual data of the first plurality of visual data of the right eye captured during a sampling time immediately prior to the sampling time of the estimated visual data; and
estimate the visual data of the left eye based on the difference and visual data of the second plurality of visual data of the left eye captured during a sampling time immediately prior to the sampling time of the estimated visual data.

12. The wearable display system of claim 9, wherein the processing electronics are further configured to estimate the visual data of the right eye or the left eye based on filtering the difference.

13. The wearable display system of claim 12, wherein filtering the difference comprises averaging.

14. A method for eye tracking, comprising:
capturing with a first camera a first plurality of visual data of a right eye at a first sampling rate;
capturing with a second camera a second plurality of visual data of a left eye at a second sampling rate, the second plurality of visual data captured during different sampling times than the first plurality of visual data; and
by processing electronics:
based on at least some visual data of the first plurality of visual data and the second plurality of visual data, estimating, as estimated visual data, visual data of at least one of the right eye or the left eye at a sampling time during which visual data of the at least one of the right eye or the left eye for which the visual data is being estimated is not being captured; and
determining eye movement of the at least one of the right eye or the left eye based on at least some of the estimated visual data and at least some visual data of the first plurality of visual data or the second plurality of visual data.

15. The method of claim 14, further comprising, by the processing electronics, causing a display to render virtual content based at least partly on the eye movement.

16. The method of claim 14, wherein determining the eye movement comprises:
determining eye movement of the right eye based on at least some of the estimated visual data of the right eye and at least some visual data of the first plurality of visual data of the right eye; and determining eye movement of the left eye based on at least some of the estimated visual data of the left eye and at least some visual data of the second plurality of visual data of the left eye.

17. The method of claim 14, wherein a combined sampling rate of the first camera and the second camera comprises an aggregate of the first sampling rate and the second sampling rate.

18. The method of claim 14, wherein the first sampling rate is equal to the second sampling rate.

19. The method of claim 14, wherein the first camera and the second camera alternately capture the first plurality of visual data and the second plurality of visual data.

20. The method of claim 14, wherein the first sampling rate and second the sampling rate comprise 30 Hz.

21. The method of claim 19, wherein a combined sampling rate of the first camera and the second camera comprises 60 Hz.

22. The method of claim 14, wherein estimating the visual data of comprises determining a difference between visual data of the first plurality of visual data of the right eye and visual data of the second plurality of visual data of the left eye.

23. The method of claim 22, wherein:
estimating the visual data of the right eye comprises determining a first difference between visual data of the second plurality of visual data of the left eye captured during the sampling time of the estimated visual data and visual data of the first plurality of visual data of the right eye captured during a sampling time prior to the sampling time of the estimated visual data; and
estimating the visual data of the left eye comprises determining a second difference between visual data of the first plurality of visual data of the right eye captured during the sampling time of the estimated visual data and visual data of the second plurality of visual data of the left eye captured during a sampling time prior to the sampling time of the estimated visual data.

24. The method of claim 23, wherein:
the sampling time of the visual data of the first plurality of visual data of the right eye is immediately prior to the sampling time of the estimated visual data; and
the sampling time of the visual data of the second plurality of visual data of the left eye is immediately prior to the sampling time of the estimated visual data.

25. The method of claim 22, further comprising, by the processing electronics:
estimating the visual data of the right eye based on the difference and visual data of the first plurality of visual data of the right eye captured during a sampling time prior to the sampling time of the estimated visual data; and
estimating the visual data of the left eye based on the difference and visual data of the second plurality of visual data of the left eye captured during a sampling time prior to the sampling time of the estimated visual data.

26. The method of claim 25, wherein:
the sampling time of the visual data of the first plurality of visual data of the right eye is immediately prior to the sampling time of the estimated visual data; and
the sampling time of the visual data of the second plurality of visual data of the left eye is immediately prior to the sampling time of the estimated visual data.

27. The method of claim 22, further comprising filtering the difference by a low pass filter.

* * * * *